US009943576B2

(12) United States Patent
Forssen et al.

(10) Patent No.: US 9,943,576 B2
(45) Date of Patent: Apr. 17, 2018

(54) FORMULATIONS OF BIOLOGICS FOR INTRAVESICAL INSTILLATION

(71) Applicant: Allergan, Inc., Irvine, CA (US)

(72) Inventors: Eric A. Forssen, La Canada, CA (US); Patrick M. Hughes, Aliso Viejo, CA (US); David C. Rupp, San Pedro, CA (US); Terrence Hunt, Menifee, CA (US); Gary Shimizu, Huntington Beach, CA (US); Joseph Francis, Aliso Viejo, CA (US); Ron S. Broide, San Marcus, CA (US); Ester Fernandez-Salas, Ann Arbor, MI (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 14/700,390

(22) Filed: Apr. 30, 2015

(65) Prior Publication Data

US 2015/0313973 A1 Nov. 5, 2015

Related U.S. Application Data

(60) Provisional application No. 61/986,346, filed on Apr. 30, 2014, provisional application No. 62/031,302, filed on Jul. 31, 2014.

(51) Int. Cl.

| | |
|---|---|
| *A61K 38/16* | (2006.01) |
| *A61K 47/10* | (2017.01) |
| *A61K 47/36* | (2006.01) |
| *A61K 38/48* | (2006.01) |
| *A61K 47/34* | (2017.01) |
| *A61K 9/00* | (2006.01) |

(52) U.S. Cl.
CPC ........ *A61K 38/4893* (2013.01); *A61K 9/0034* (2013.01); *A61K 38/164* (2013.01); *A61K 47/10* (2013.01); *A61K 47/34* (2013.01); *A61K 47/36* (2013.01); *C12Y 304/24069* (2013.01)

(58) Field of Classification Search
CPC ...... A61K 38/164; A61K 47/10; A61K 47/34; A61K 47/36
See application file for complete search history.

(56) References Cited

U.S. PATENT DOCUMENTS

| | | |
|---|---|---|
| 7,449,192 B2 | 11/2008 | Schmidt |
| 7,892,565 B2 | 2/2011 | Steward |
| 8,168,206 B1 | 5/2012 | Hunt |
| 8,198,034 B2 | 6/2012 | Fernandez-Salas et al. |
| 8,361,789 B2 | 1/2013 | Zhu et al. |
| 8,512,992 B2 | 8/2013 | Steward et al. |
| 2005/0244358 A1* | 11/2005 | Hermida Ochoa .. A61K 9/0024 424/70.13 |
| 2008/0241881 A1 | 10/2008 | Steward |
| 2009/0069238 A1 | 3/2009 | Steward |
| 2009/0081730 A1 | 3/2009 | Dolly |
| 2009/0214685 A1* | 8/2009 | Hunt ................... A61K 9/0024 424/780 |
| 2010/0203559 A1 | 8/2010 | Fernandez-Salas |
| 2010/0233741 A1 | 9/2010 | Wang |
| 2010/0233802 A1 | 9/2010 | Zhu et al. |
| 2011/0189162 A1 | 8/2011 | Ghanshani |
| 2011/0280952 A1* | 11/2011 | Caramella ............. A61K 9/006 424/530 |
| 2012/0136055 A1* | 5/2012 | Stensrud ............. A61K 9/0031 514/551 |
| 2012/0189677 A1 | 7/2012 | Tonge |
| 2013/0251770 A1* | 9/2013 | Waugh ................... A61Q 19/08 424/401 |

FOREIGN PATENT DOCUMENTS

| | | | |
|---|---|---|---|
| BR | 201005054 A2 | * | 4/2013 |
| JP | 2005-306746 A | * | 11/2005 |
| WO | WO2010-090677 | | 8/2010 |
| WO | WO 2010/090677 A1 | * | 8/2010 |
| WO | WO2011-022272 | | 2/2011 |
| WO | 2013-0153550 | | 10/2013 |
| WO | WO 2013/153550 A2 | * | 10/2013 |
| WO | WO 2014/184746 A1 | * | 11/2014 |

OTHER PUBLICATIONS

Lee et al. Development and evaluation of a mucoadhesive drug delivery system for dual-controlled delivery of Nonoxynol-9. Journal of Controlled Release. 1996. vol. 39, pp. 93-103.*
Barthelmes, Jan et al, Development of Mucoadhesive Nanoparticulate Drug Delivery System for a Targeted Drug Release in the Bladder, International Journal of Pharmaceutics, 2011, 339-345, 416.
Giannantoni, Antonella et al, New Frontiers in Intravesical Therapies and Drug Delivery, European Urology, 2006, 1183-1193, 50.
Khutoryanskiy, Vitaliy, Advances in Mucoadhesion and Mucoadhesive Polymers, Macromolecular Bioscience, 2011, 748-764, 11.
Ansel, Howard, Pharmaceutical Dosage Forms and Drug Delivery Systems, 1999, Williams & Wilkins, 2 Pages, 7th edition, Lippincott.
Fernandez-Salas, Ester et al, Botulinum Neurotoxin Serotype a Specific Cell-Based Potency Assay to Replace the Mouse Bioassay, PLOS ONE, Nov. 2012, 1-13, 7 (11).
Gennaro, Remington, Ophthalmic Preparations—Vehicles, The Science and Practice of Pharmacy, 2000, 827, 20th Edition.
Harman, Joel G, Goodman & Gilman's the Pharmacological Basis of Therapeutics, 10th Edition, McGraw-Hill, 2001, 2 pages.
Hunt, Terrence et al., Characterization of SNARE Cleavage Products Generated by Formulated Botulinum Neurotoxin Type-A drug Products, TOXINS 2010, 2, 2198-2212.
Rowe, Raymond et al, Aliphatic Polyesters, Handbook of Pharmaceutical Excipients, Nov. 2003, 19-21, 4th Edition.

* cited by examiner

*Primary Examiner* — Jeffrey E. Russel
(74) *Attorney, Agent, or Firm* — Brigitte C. Phan; Ted A. Chan

(57) ABSTRACT

Pharmaceutical formulations comprising a clostridial derivative and a permeabilizing agent for intravesical instillation are disclosed.

9 Claims, 20 Drawing Sheets
(17 of 20 Drawing Sheet(s) Filed in Color)

BOTOX® (Complex or Dissociated) in transport is equivalent to Surrogate based on pH study.
Average scores from normal bladders instilled with BOTOX® (20 U)
at either pH 6.0 or pH 8.0
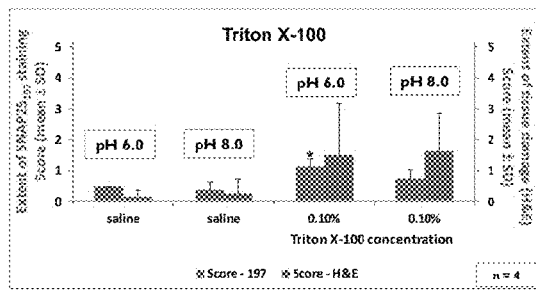
- BoNT/A 900 complex is completely dissociated at pH 8 releasing within normal limits minimal mixed cell infiltrates
minimal spindle cell infiltrates mild mixed cell inflammation
mild spindle cell infiltrates moderate mixed cell inflammation
moderate spindle cell infiltrates
ulceration

* Statistically significant difference with the group of 0.1% Tyloxapol.

FORMULATIONS OF BIOLOGICS FOR INTRAVESICAL INSTILLATION

CROSS-REFERENCES TO RELATED APPLICATIONS

This application claims the benefit of U.S. Provisional Application Ser. Nos. 61/986,346, filed Apr. 30, 2014, and 62/031,302, filed Jul. 31, 2014, all incorporated herein entirely by reference.

FIELD OF INVENTION

The present disclosure relates to pharmaceutical formulations comprising a clostridial derivative and methods of use thereof. In particular, the present disclosure relates to pharmaceutical formulations containing a clostridial derivative for bladder instillation.

BACKGROUND

Neurotoxin therapies, in particular botulinum toxins, have been used in treatments of various medical conditions, including urological conditions such as overactive bladder (OAB) and detrusor overactivity.

Botulinum toxin therapy to treat bladder disorders such as overactive bladder (OAB), detrusor overactivity associated with a neurological condition, is typically administered by injection across the urinary bladder wall and into the enervated muscular tissues surrounding the bladder. This approach requires administering about thirty to forty injections through the bladder wall, as shown in FIG. 1. Pharmaceutical administration by injection may cause localized pain, and potentially expose patients to blood borne diseases. Among alternative administration routes, intravesical instillation allows a drug to be delivered directly into the bladder by crossing the bladder wall.

The bladder wall is impermeable to most substances. As shown in FIG. 2, the stratified urothelium consists of three cellular layers: umbrella cells, intermediate cells, and basal cells. The basal cells are germinal cells that through cell division replace intermediate cells that are partially differentiated. The highly differentiated and polarized umbrella cells are located on the lumen of the bladder and are the primary physical barrier to the movement of substances between the blood and urine. The apical membrane of the umbrella cells is covered with plaques consisting of proteins called uroplakins and gives the apical membrane a thick appearance. The umbrella cells also contain tight junctions that restrict the paracellular movement of urine and larger molecules through the epithelium.

Thus, there remains a need for pharmaceutical formulations containing a clostridial derivative that can enhance delivery across the urinary bladder wall in lieu of parenteral administration.

Clostridial toxin therapies are successfully used for many indications. Generally, administration of a Clostridial toxin treatment is well tolerated. It has been found that botulinum toxins are able to affect many different types of neurons in the human body, but for the treatment of some medical conditions, more specific molecules will be advantageous. Thus, there remains a need for pharmaceutical formulations containing modified clostridial derivatives, such as Targeted Exocytosis Modulators (TEMs), targeted for specific types of neuronal cells.

SUMMARY OF THE INVENTION

In some aspects, the present disclosure provides pharmaceutical formulations for intravesical (urinary bladder) administration, comprising a clostridial derivative and at least one permeabilizing agent, which can permeate the bladder wall of a patient and retain the clostridial derivative's bioactivity to cause a desired therapeutic effect.

In one aspect, the present disclosure provides a pharmaceutical composition comprising a therapeutically effective amount of a clostridial derivative and at least one permeabilizing agent, wherein the at least one permeabilizing agent is present in an amount effective to substantially and reversibly increase the permeability of the bladder wall to the clostridial derivative.

In another aspect, the present disclosure provides a method for making a pharmaceutical formulation suitable for intravesical bladder administration, the method comprising providing a solution comprising at least one permeabilizing agent; adding the solution to a composition comprising a clostridial derivative. In some embodiments, the method comprises adding about 50 ml to about 100 ml of the solution to the clostridial derivative. In some embodiments, the clostridial derivative is a botulinum toxin. In one embodiment, the method comprises adding about 50 ml to about 100 ml of an aqueous solution comprising about 1% (w/v) chitosan, analogs or derivatives and about 0.1% (w/v) Triton™X-100, analogs or derivatives, to a botulinum toxin type A. In one embodiment, the method comprises adding a 50 ml aqueous solution comprising 1% (w/v) chitosan and 0.1% (w/v) Triton™X-100 to a vial containing about 100 Units or 200 Units of a lyophilized botulinum toxin type A; and mixing gently to rehydrate the lyophilized botulinum toxin type A.

In another aspect, the present pharmaceutical formulation maximizes the bioavailability of the clostridial derivative by preventing or minimizing the adsorption of the clostridial derivative to catheters, deliver device surfaces (syringe, patch, microneedle, engineered injector (Bioject, etc.), tubing and containers.

According to another aspect, the present disclosure provides methods for treating medical disorders in a patient, the methods comprise the step of administering a pharmaceutical composition provided in accordance with the present disclosure, thereby treating the medical disorders. In one embodiment, the present methods alleviate one or more symptoms of the medical disorders. In one embodiment, the medical disorders include neurogenic idiopathic bladder dysfunction, or bladder pain. In some aspects, a method is provided for treating a patient with a neurogenic or idiopathic bladder dysfunction, bladder pain, comprising: intravesically instilling into the bladder of the patient a pharmaceutical composition comprising a therapeutically effective amount of a clostridial derivative and at least one permeabilizing agent present in an amount effective to substantially increase the permeability of the bladder wall to the clostridial derivative at a therapeutically effective rate.

Other aspects and variations of the present pharmaceutical formulations and methods summarized above are also contemplated and will be more fully understood when considered with respect to the following disclosure.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 2 is a schematic of the urothelium, wherein:

A) The urothelium consists of three cell layers: basal, intermediate, and superficial umbrella cells.
B) The umbrella cells display plaques on their apical membrane and a cytoplasmic network of vesicles containing fibrils joined at the tight junction and the desmosomes on the smooth basal membrane.
C) The apical membrane of the urothelium viewed for the lumen shows the plaque and hinge regions.

Figure 1:
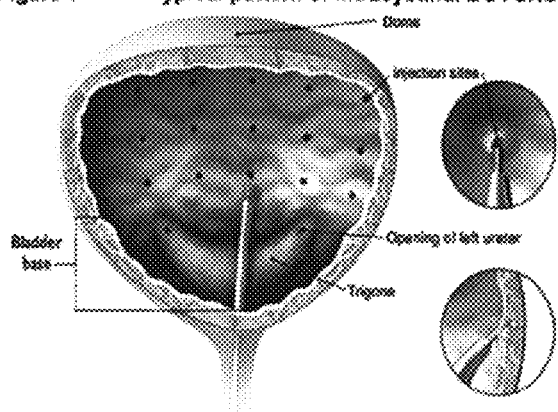
FIG. 1 shows a prior art intracystinal injection of a botulinum toxin to the bladder wall.
Figure 2:
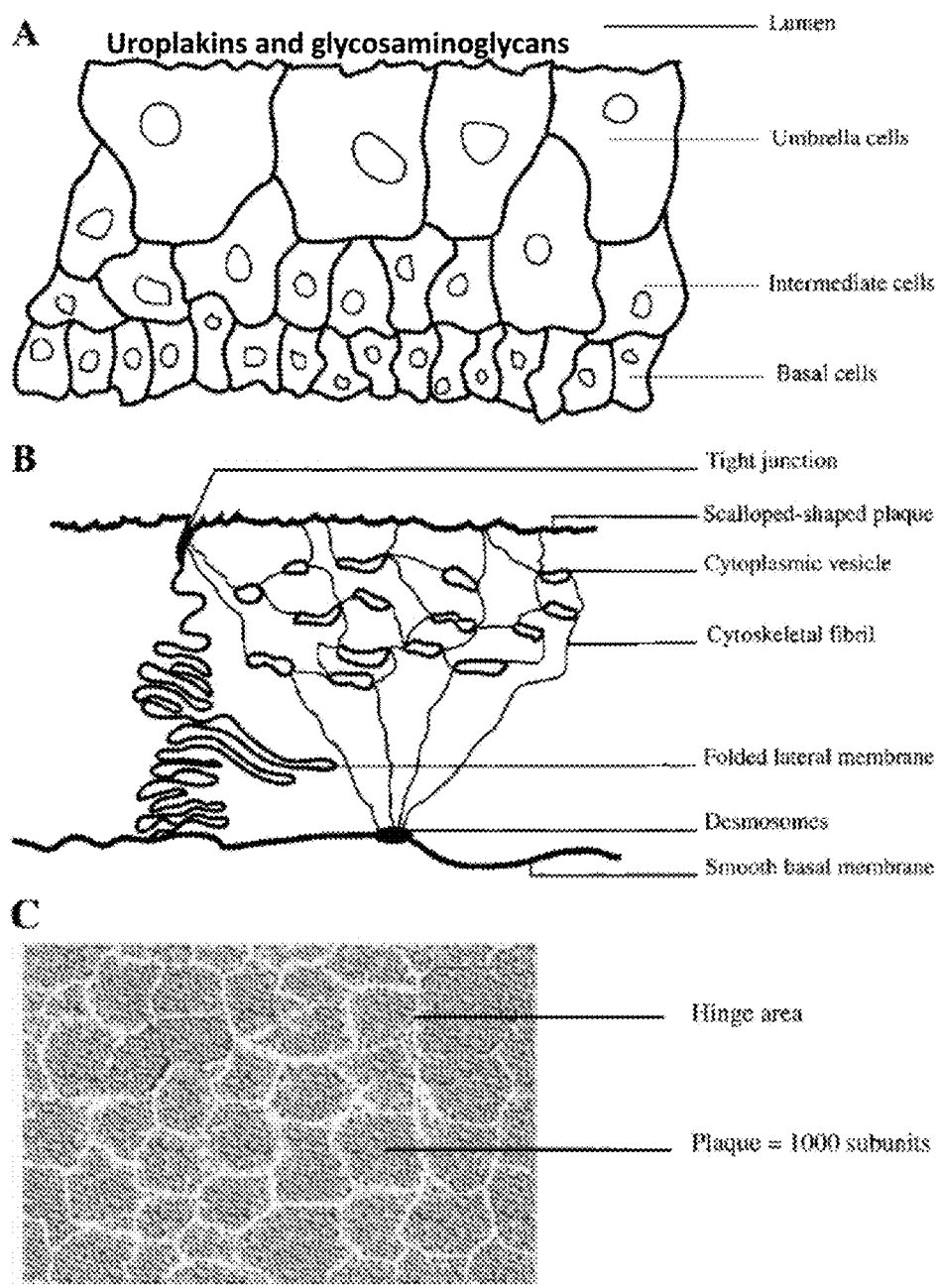
Figure 3:
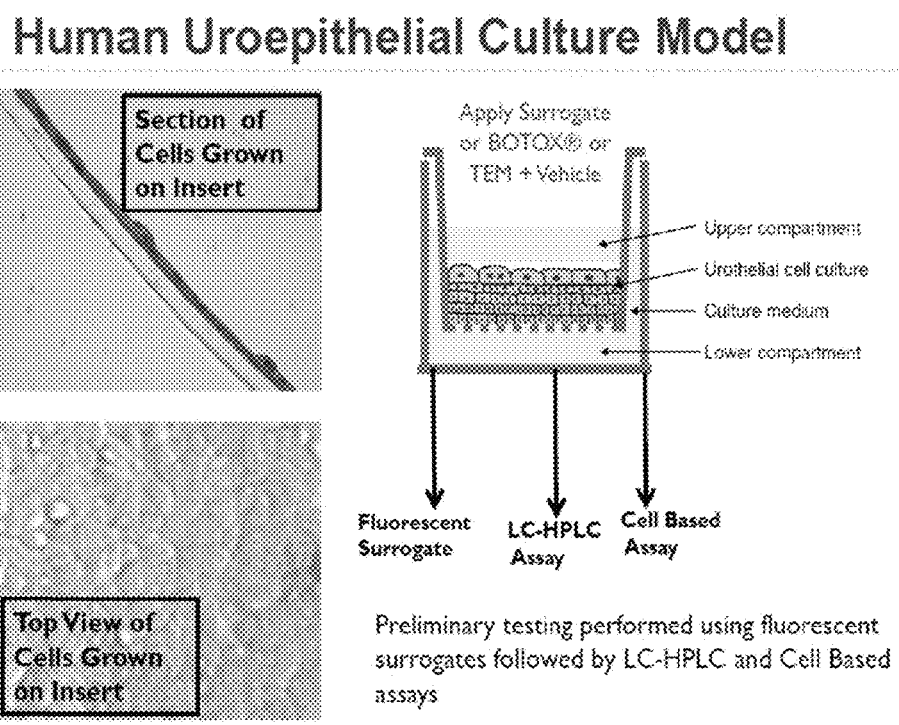
Figure 4:
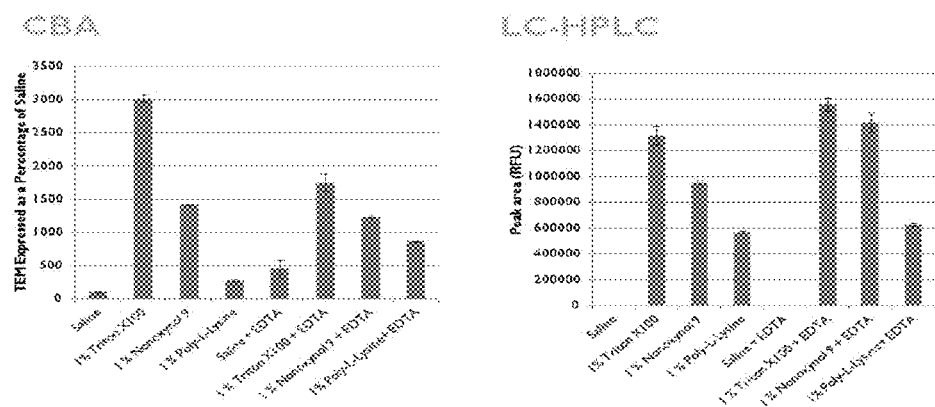
Figure 5A:
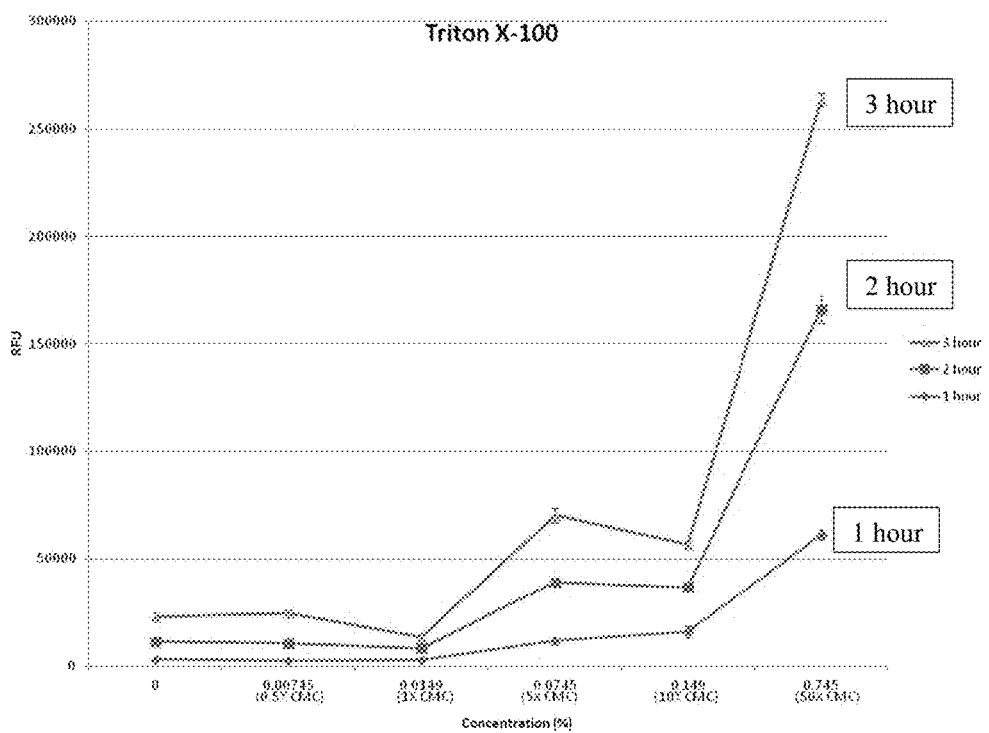
Figure 5B:
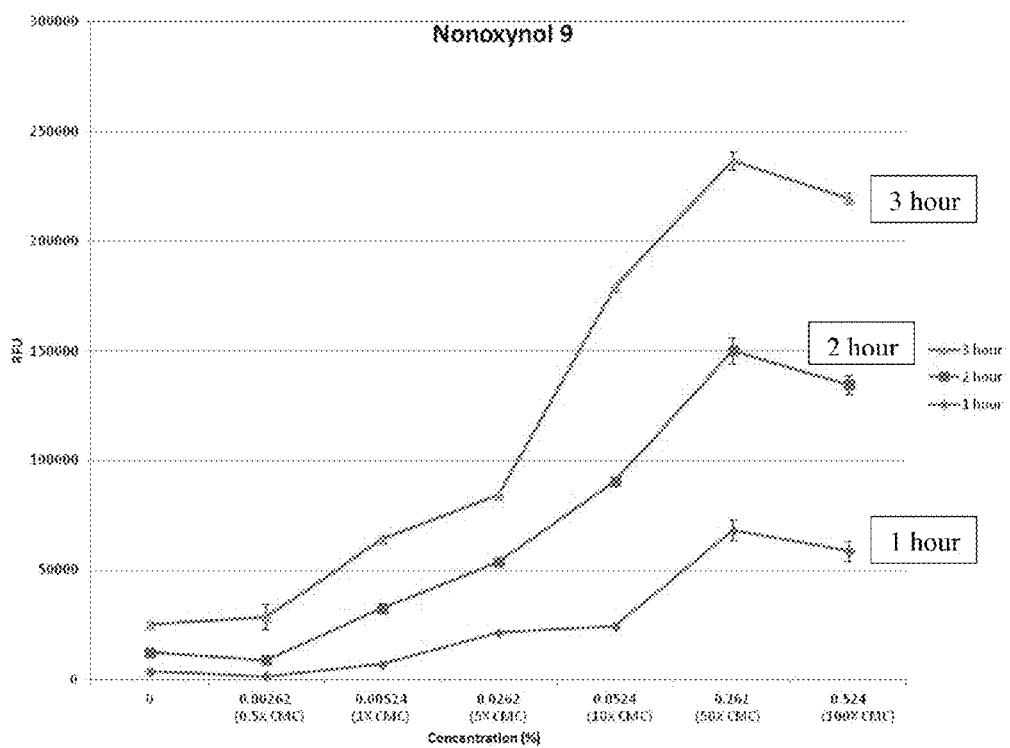
Figure 6A:
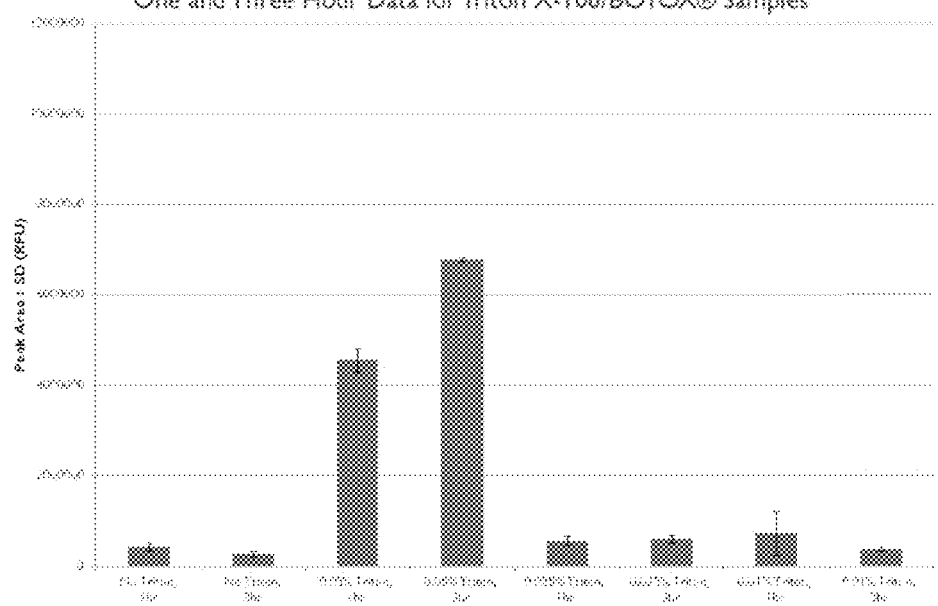
Figure 6B:
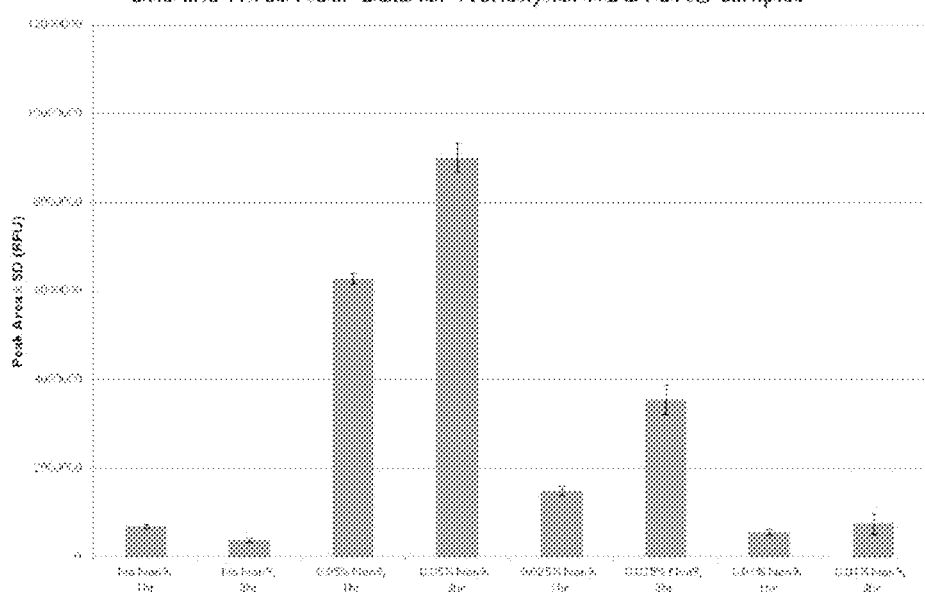
Figure 7:
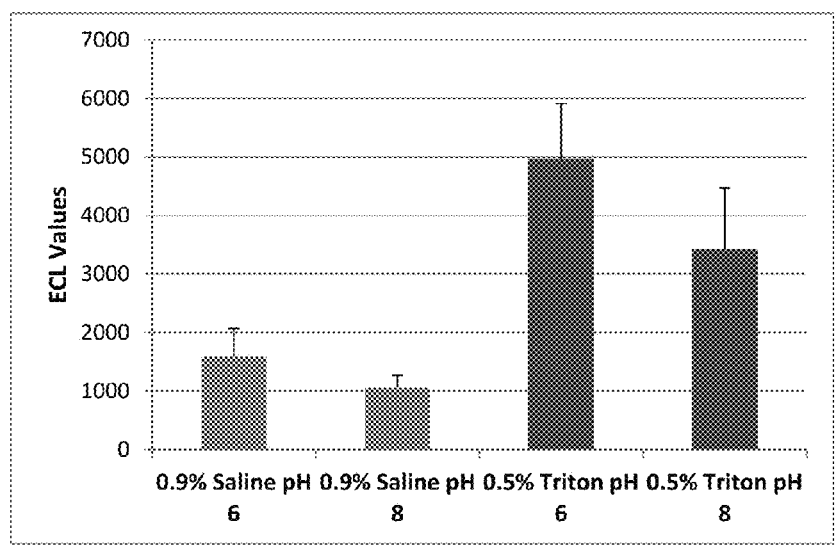
Figure 8A:
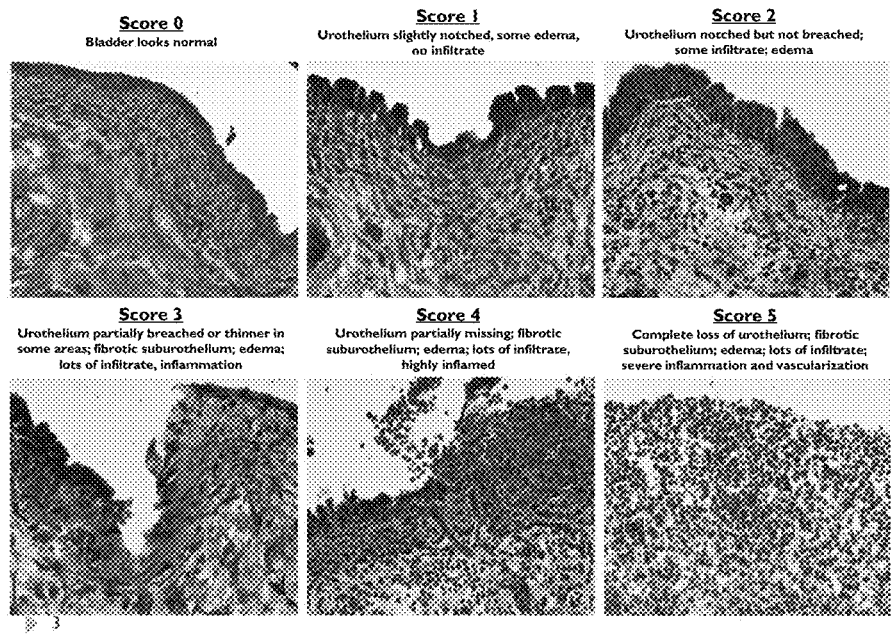
Figure 8B:
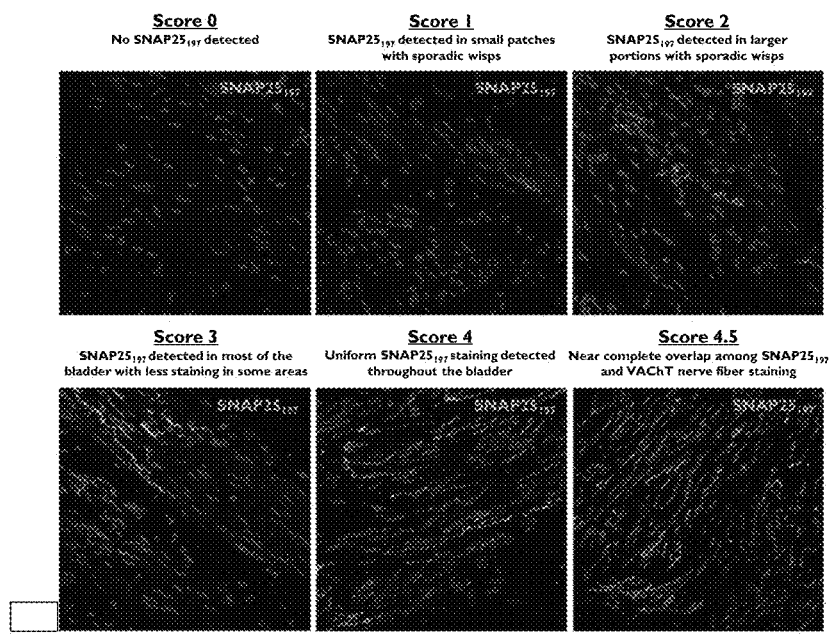
Figure 9A:
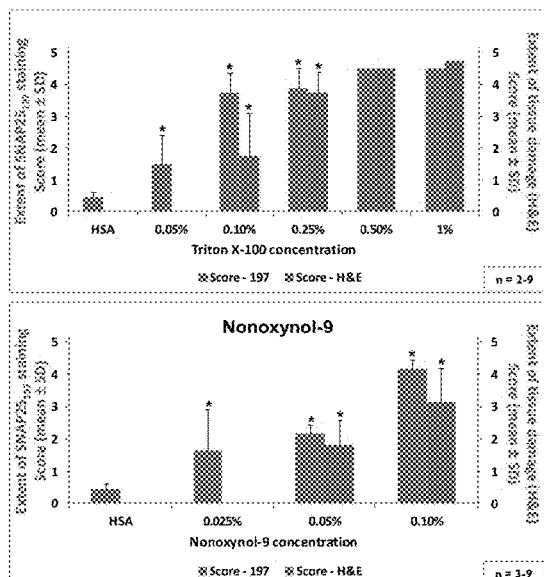

FIG. 3 shows a schematic of the human uroepithelial culture model; a diagram of the Transwell® permeable support system with a stratified urothelium;

FIG. 4 shows an exemplary graph displaying differential effect of various permeabilizing agents on the permeability of human uroepithelial cells to an exemplary surrogate;

FIGS. 5A and 5B show concentration and time dependent effects of two exemplary permeabilizing agents on the cell permeability and Light chain activity of an exemplary TEM surrogate;

FIGS. 6A and 6B show concentration and time dependent effects of two exemplary permeabilizing agents on the cell permeability and Light chain activity of a botulinum toxin type A;

FIG. 7 shows the effect of an exemplary permeabilizing agent on the cell permeability and Light chain activity of a botulinum toxin type A at pH 6.0 or 8.0;

FIGS. 8-10 display data obtained in vivo, wherein effect of exemplary formulations in accordance of the present disclosure was quantified in rats;

FIG. 8A is a pictorial diagram establishing a basis for assessing rat bladder integrity, using an ordinal scoring method of 0-5; '0' being a normal bladder and '5' showing severe pathology;

FIG. 8B is a pictorial diagram showing a basis for assessing the penetration of an exemplary surrogate into the bladder wall. The assessment relies on the extent of SNAP25-197 staining corresponding to VAChT staining of parasympathetic nerve fibers in rat bladder using an ordinal scoring method of 0-5; '0' being no SNAP25-197 staining detected and '4.5' showing near complete overlap of both biomarkers. A score of '5' was never observed;

FIG. 9A shows the effect of an exemplary formulation comprising an exemplary surrogate in accordance with aspect of the present disclosure following instillation into normal bladders, as measured by: (1) the extent of penetration of the surrogate at various concentrations of exemplary permeabilizing agents; and (2) bladder tissue integrity. The extent of penetration was correlated to the extent of SNAP25-197 staining (blue bars, or first bar of two contiguous bars) and the bladder tissue damage was based on H&E staining (red bars, or second bar of two contiguous bars). The bars without an adjoining bar show extent of SNAP25-197 staining.

Figure 9B:
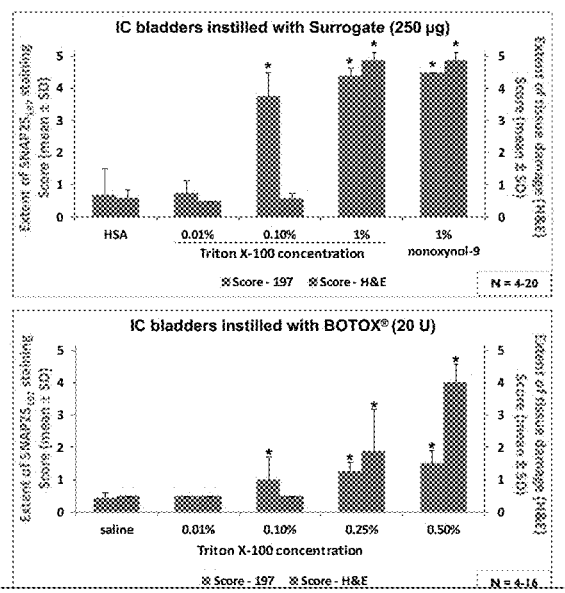
Figure 11:
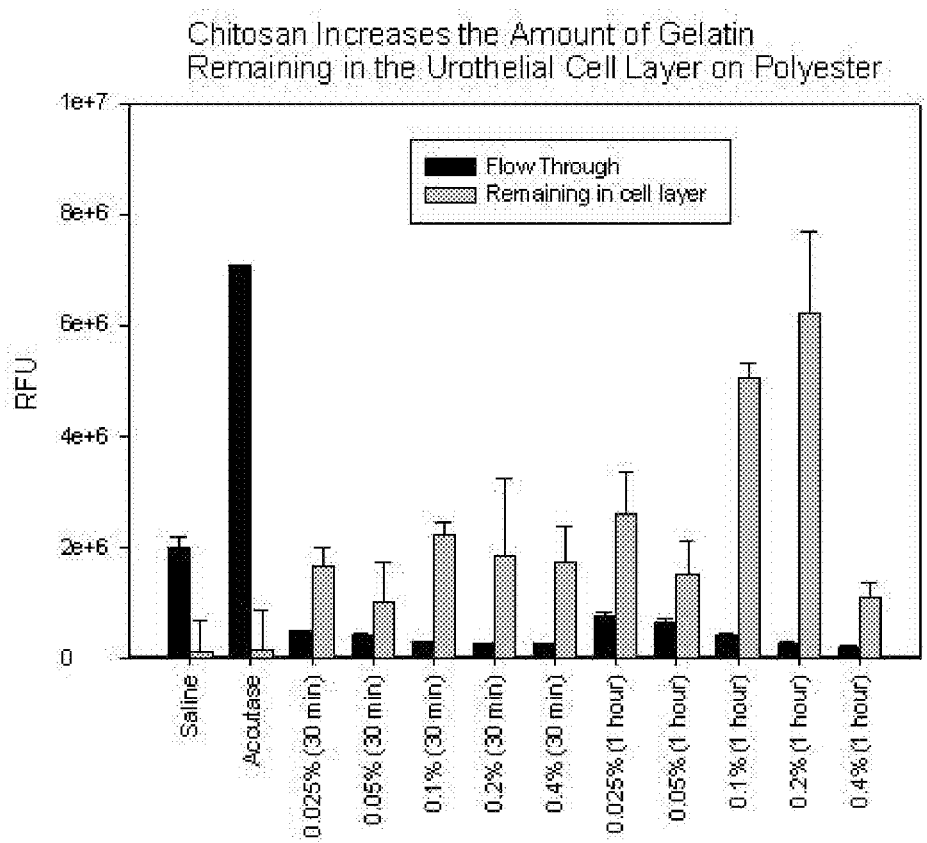

FIG. 9B shows the effect of the exemplary formulation following instillation into bladders from Interstitial cystitis (IC) model, as measured by: (1) the extent of penetration of an exemplary surrogate at various concentrations of exemplary permeabilizing agents; and (2) bladder tissue integrity. The extent of penetration was correlated to the extent of SNAP25-197 staining (blue bars, or first bar of two contiguous bars) and the bladder tissue damage was based on H&E staining (red bars, or second bar of two contiguous bars);

FIG. 10 shows the effect of an exemplary formulation comprising a botulinum toxin complex (20 U) following instillation into normal bladders at pH 6.0 or 8.0, as measured by: (1) the extent of penetration of the botulinum toxin complex at various concentrations of an exemplary permeabilizing agent; and (2) bladder tissue integrity. The extent of penetration was correlated to the extent of SNAP25-197 staining (blue bars, or first bar of two contiguous bars) and the bladder tissue damage was based on H&E staining (red bars, or second bar of two contiguous bars); and FIG. 11 shows the effect of an exemplary permeabilizing agent on the mucoadhesion of a surrogate.

Figure 12:
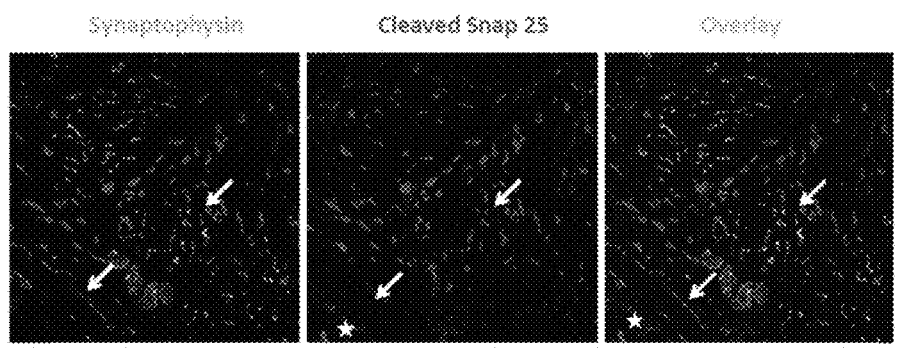
Figure 13:
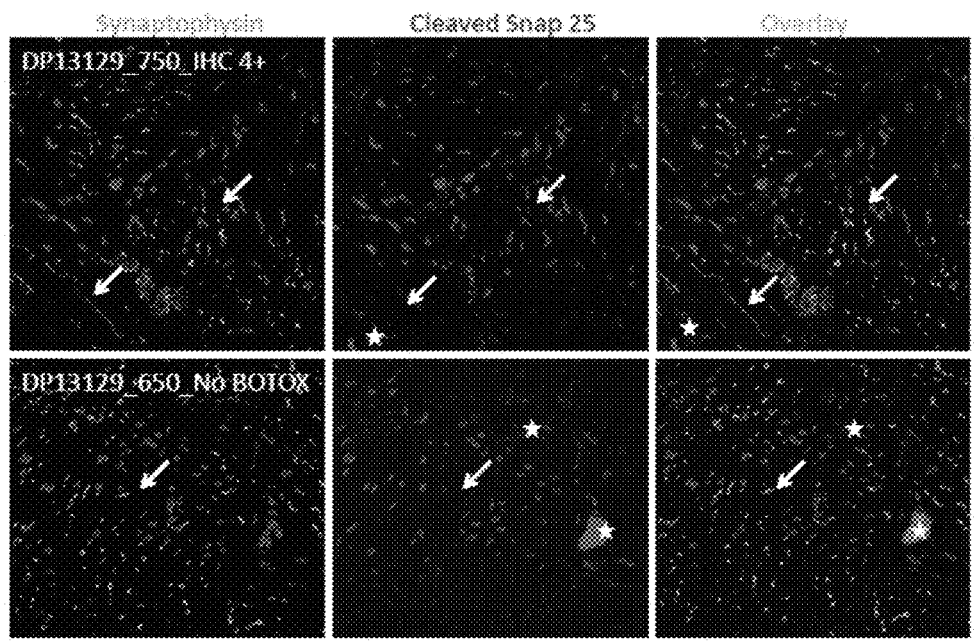
Figure 14A:
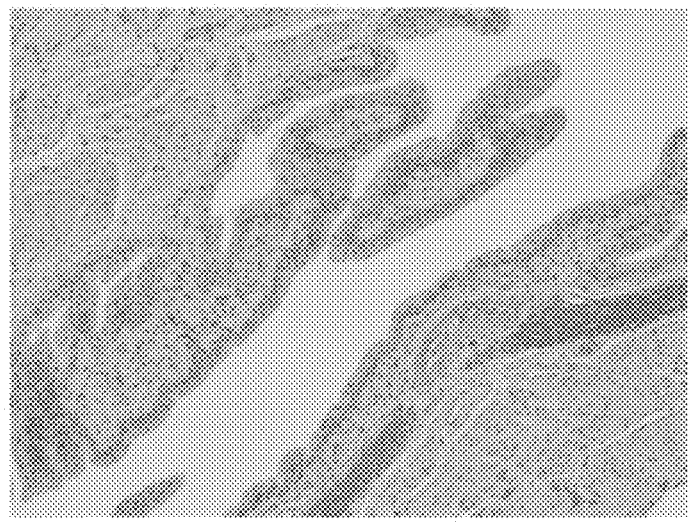
Figure 14B:
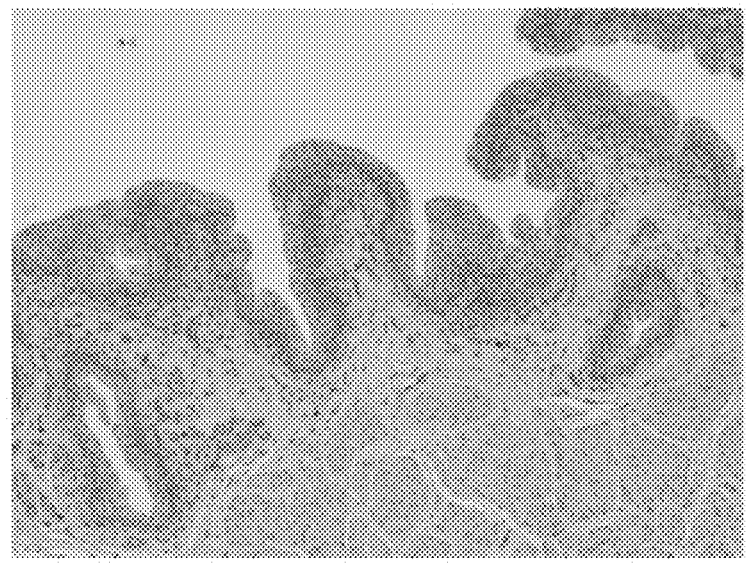
Figure 14C:
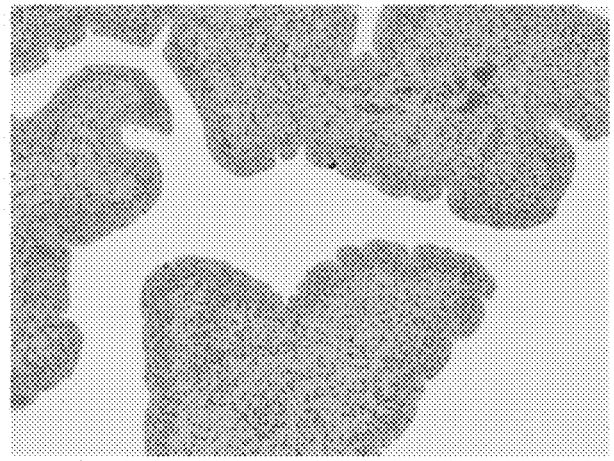
Figure 14D:
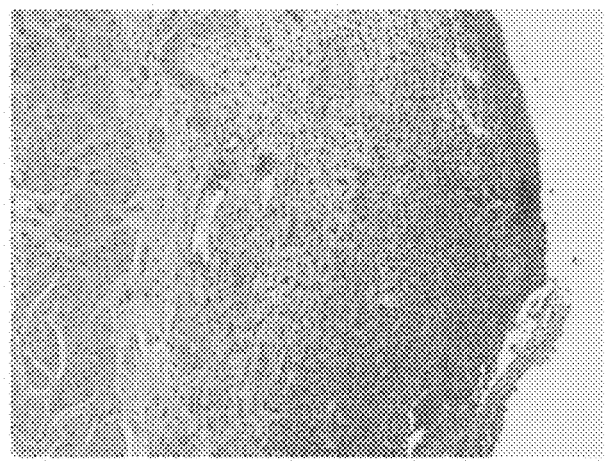
Figure 15:
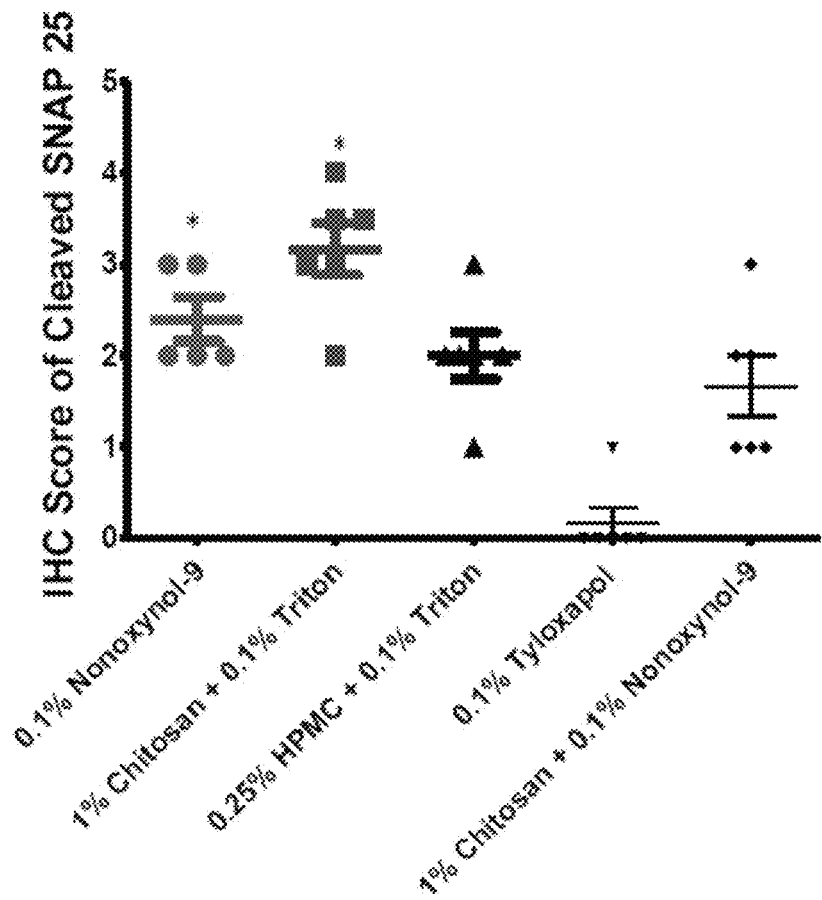

FIG. 12 is a pictorial diagram establishing a basis for assessing the extent of penetration into the bladder of a test formulation. The extent of penetration was correlated to the extent of SNAP25-197 staining;

FIG. 13 is a pictorial diagram showing exemplary immunohistochemistry results from two bladders having IHC scores of "4" and "0";

FIGS. 14A-D are illustrative photomicrographs showing different states of the bladder tissue after instillation; and FIG. 15 is a graph displaying the immunohistochemistry (IHC) scores of some exemplary formulations according to aspects of the present disclosure.

DESCRIPTION

Botulinum neurotoxins (BoNTs), for example, BoNT/A, BoNT/B, etc., act on the nervous system by blocking the release of neurosecretory substances including neurotransmitters. The action of BoNT is initiated by its binding to a receptor molecule on the cell surface. The resulting toxin-receptor complex then undergoes endocytosis. Once inside the cell, BoNT cleaves exocytotic specific proteins responsible for neurotransmitter docking and release from the cell known as the SNARE proteins (soluble N-ethylmaleimide-sensitive factor attachment protein receptor). The resulting transient chemodenervation has been utilized medically to block motor neurotransmission at the neuromuscular junction, leading to a variety of therapeutic applications.

Aspects of the present disclosure provide, in part, a pharmaceutical formulation suitable for intravesical bladder delivery, comprising a clostridial derivative and at least one permeabilizing agent.

In one aspect, the present disclosure provides in part a pharmaceutical composition comprising a therapeutically effective amount of a clostridial derivative and at least one permeabilizing agent, wherein the at least one permeabilizing agent is present in an amount effective to substantially and reversibly increase the permeability of the bladder wall to the clostridial derivative. In some embodiments, the clostridial derivative is a botulinum toxin. In some embodiments, the at least one permeabilizing agent comprises a surfactant and a mucoadhesive.

Definitions

As used herein, the words or terms set forth below have the following definitions:

"About" or "approximately" as used herein means within an acceptable error range for the particular value as determined by one of ordinary skill in the art, which will depend in part on how the value is measured or determined, (i.e., the limitations of the measurement system). For example, "about" can mean within 1 or more than 1 standard deviations, per practice in the art. Where particular values are described in the application and claims, unless otherwise stated, the term "about" means within an acceptable error range for the particular value.

"Active pharmaceutical ingredient" (API) means an ingredient that exerts an effect upon or after administration to a subject or patient. API's can include, for example, a native or recombinant, clostridial neurotoxin, e.g. a botulinum toxin, recombinant modified toxins, fragments thereof, TEMs, and combinations thereof.

"Administration", or "to administer" means the step of giving (i.e. administering) a pharmaceutical composition to a subject, or alternatively a subject receiving a pharmaceutical composition. The pharmaceutical compositions disclosed herein can be locally administered by various methods. For example, intramuscular, intradermal, subcutaneous administration, intrathecal administration, intraperitoneal administration, topical (transdermal), instillation, and implantation (for example, of a slow-release device such as polymeric implant or miniosmotic pump) can all be appropriate routes of administration.

"Alleviating" means a reduction in the occurrence of a pain, of a headache, of a hyperactive muscle, or of any symptom or cause of a condition or disorder. Thus, alleviating includes some reduction, significant reduction, near total reduction, and total reduction.

"Animal protein free" means the absence of blood derived, blood pooled and other animal derived products or compounds. "Animal" means a mammal (such as a human), bird, reptile, fish, insect, spider or other animal species. "Animal" excludes microorganisms, such as bacteria. Thus, an animal protein free pharmaceutical composition can include a botulinum neurotoxin, a recombinant modified toxin, or a TEM. For example, an "animal protein free" pharmaceutical composition means a pharmaceutical composition which is either substantially free or essentially free or entirely free of a serum derived albumin, gelatin and other animal derived proteins, such as immunoglobulins. An example of an animal protein free pharmaceutical composition is a pharmaceutical composition which comprises or which consists of a botulinum toxin, a TEM, or a recombinant modified toxin (as the active ingredient) and a suitable polysaccharide as a stabilizer or excipient.

"Biological activity" describes the beneficial or adverse effects of a drug on living matter. When a drug is a complex chemical mixture, this activity is exerted by the substance's active ingredient but can be modified by the other constituents. Biological activity can be assessed as potency or as toxicity by an in vivo $LD_{50}$ or $ED_{50}$ assay, or through an in vitro assay such as, for example, cell-based potency assays as described in U.S. publications 20100203559, 20100233802, 20100233741 and U.S. Pat. No. 8,198,034, each of which is hereby incorporated by reference in its entirety.

"Botulinum toxin" means a neurotoxin produced by *Clostridium botulinum*, as well as a botulinum toxin (or the light chain or the heavy chain thereof) made recombinantly by a non-Clostridial species. The phrase "botulinum toxin", as used herein, encompasses the botulinum toxin serotypes A, B, C, D, E, F and G, and their subtypes and any other types of subtypes thereof, or any re-engineered proteins, analogs, derivatives, homologs, parts, sub-parts, variants, or versions, in each case, of any of the foregoing. "Botulinum toxin", as used herein, also encompasses a "modified botulinum toxin". Further "botulinum toxin" as used herein also encompasses a botulinum toxin complex, (for example, the 300, 500 and 900 kDa complexes), as well as the neurotoxic component of the botulinum toxin (150 kDa) that is unassociated with the complex proteins.

"Clostridial derivative" refers to a molecule which contains any part of a clostridial toxin. As used herein, the term "clostridial derivative" encompasses native or recombinant neurotoxins, recombinant modified toxins, fragments thereof, a Targeted vesicular Exocytosis Modulator (TEM), or combinations thereof.

"Clostridial toxin" refers to any toxin produced by a Clostridial toxin strain that can execute the overall cellular mechanism whereby a Clostridial toxin intoxicates a cell and encompasses the binding of a Clostridial toxin to a low or high affinity Clostridial toxin receptor, the internalization of the toxin/receptor complex, the translocation of the Clostridial toxin light chain into the cytoplasm and the enzymatic modification of a Clostridial toxin substrate. Non-limiting examples of Clostridial toxins include a Botulinum toxin like BoNT/A, a BoNT/B, a BoNT/$C_1$, a BoNT/D, a BoNT/E, a BoNT/F, a BoNT/G, a Tetanus toxin (TeNT), a Baratii toxin (BaNT), and a Butyricum toxin (BuNT). The BoNT/$C_2$ cytotoxin and BoNT/$C_3$ cytotoxin, not being neurotoxins, are excluded from the term "Clostridial toxin." A Clostridial toxin disclosed herein includes, without limitation, naturally occurring Clostridial toxin variants, such as, e.g., Clostridial toxin isoforms and Clostridial toxin subtypes; non-naturally occurring Clostridial toxin variants, such as, e.g., conservative Clostridial toxin variants, non-conservative Clostridial toxin variants, Clostridial toxin chimeric variants and active Clostridial toxin fragments thereof, or any combination thereof. A Clostridial toxin disclosed herein also includes a Clostridial toxin complex. As used herein, the term "Clostridial toxin complex" refers to a complex comprising a Clostridial toxin and non-toxin associated proteins (NAPs), such as, e.g., a Botulinum toxin complex, a Tetanus toxin complex, a Baratii toxin complex, and a Butyricum toxin complex. Non-limiting examples of Clostridial toxin complexes include those produced by a *Clostridium botulinum*, such as, e.g., a 900-kDa BoNT/A complex, a 500-kDa BoNT/A complex, a 300-kDa BoNT/A complex, a 500-kDa BoNT/B complex, a 500-kDa BoNT/$C_1$ complex, a 500-kDa BoNT/D complex, a 300-kDa BoNT/D complex, a 300-kDa BoNT/E complex, and a 300-kDa BoNT/F complex.

""Effective amount" as applied to the biologically active ingredient means that amount of the ingredient which is generally sufficient to induce a desired change in the subject. For example, where the desired effect is a reduction in an autoimmune disorder symptom, an effective amount of the ingredient is that amount which causes at least a substantial reduction of the autoimmune disorder symptom, and without resulting in significant toxicity.

"Effective amount" as applied to a non-active ingredient constituent of a pharmaceutical composition (such as a stabilizer used for mixing with a botulinum toxin) refers to that amount of the non-active ingredient constituent which is sufficient to positively influence the release and/or activity of the active ingredient when administered to an individual. This "effective amount" can be determined based on the teaching in this specification and the general knowledge in the art.

"Entirely free (i.e. "consisting of" terminology) means that within the detection range of the instrument or process being used, the substance cannot be detected or its presence cannot be confirmed.

"Essentially free" (or "consisting essentially of") means that only trace amounts of the substance can be detected.

"Light chain" means the light chain of a clostridial neurotoxin. It has a molecular weight of about 50 kDa, and can be referred to as the L chain, L, or as the proteolytic domain (amino acid sequence) of a botulinum neurotoxin.

"Heavy chain" means the heavy chain of a botulinum neurotoxin. It has a molecular weight of about 100 kDa and can be referred to as the H chain, or as H.

$H_C$ means a fragment (about 50 kDa) derived from the H chain of a botulinum neurotoxin which is approximately equivalent to the carboxyl end segment of the H chain, or the portion corresponding to that fragment in the intact H chain. It is believed to contain the portion of the natural or wild type botulinum neurotoxin involved in high affinity, presynaptic binding to motor neurons.

$H_N$ means a fragment (about 50 kDa) derived from the H chain of a botulinum neurotoxin which is approximately equivalent to the amino end segment of the H chain, or a portion corresponding to that fragment. It is believed to contain the portion of the natural or wild type botulinum neurotoxin involved in the translocation of the L chain across an intracellular endosomal membrane.

$LH_N$ or $L-H_N$ means a fragment derived from a clostridial neurotoxin that contains the L chain, or a functional fragment thereof coupled to the $H_N$ domain. It can be obtained from the intact clostridial neurotoxin by proteolysis, so as to remove or to modify the $H_C$ domain.

"Implant" means a controlled release (e.g., pulsatile or continuous) composition or drug delivery system. The implant can be, for example, injected, inserted or implanted into a human body.

"Intravesical administration" refers to the injection of a given substance directly into the bladder via a urethral catheter.

"Local administration" means direct administration of a pharmaceutical at or to the vicinity of a site on or within an animal body, at which site a biological effect of the pharmaceutical is desired, such as via, for example, intramuscular or intra- or subdermal injection or topical administration. Local administration excludes systemic routes of administration, such as intravenous or oral administration. Topical administration is a type of local administration in which a pharmaceutical agent is applied to a patient's skin.

"Modified botulinum toxin" means a botulinum toxin that has had at least one of its amino acids deleted, modified, or replaced, as compared to a native botulinum toxin. Additionally, the modified botulinum toxin can be a recombinantly produced neurotoxin, or a derivative or fragment of a recombinantly made neurotoxin. A modified botulinum toxin retains at least one biological activity of the native botulinum toxin, such as, the ability to bind to a botulinum toxin receptor, or the ability to inhibit neurotransmitter release from a neuron. One example of a modified botulinum toxin is a botulinum toxin that has a light chain from one botulinum toxin serotype (such as serotype A), and a heavy chain from a different botulinum toxin serotype (such as serotype B). Another example of a modified botulinum toxin is a botulinum toxin coupled to a neurotransmitter, such as substance P.

"Mutation" means a structural modification of a naturally occurring protein or nucleic acid sequence. For example, in the case of nucleic acid mutations, a mutation can be a deletion, addition or substitution of one or more nucleotides in the DNA sequence. In the case of a protein sequence mutation, the mutation can be a deletion, addition or substitution of one or more amino acids in a protein sequence. For example, a specific amino acid comprising a protein sequence can be substituted for another amino acid, for example, an amino acid selected from a group which includes the amino acids alanine, asparagine, cysteine, aspartic acid, glutamic acid, phenylalanine, glycine, histidine, isoleucine, lysine, leucine, methionine, proline, glutamine, arginine, serine, threonine, valine, tryptophan, tyrosine or any other natural or non-naturally occurring amino acid or chemically modified amino acids. Mutations to a protein sequence can be the result of mutations to DNA sequences that when transcribed, and the resulting mRNA translated, produce the mutated protein sequence. Mutations to a protein sequence can also be created by fusing a peptide sequence containing the desired mutation to a desired protein sequence.

"Patient" means a human or non-human subject receiving medical or veterinary care. Accordingly, as disclosed herein, the compositions and methods can be used in treating any animal, such as, for example, mammals, or the like.

"Peripherally administering" or "peripheral administration" means subdermal, intradermal, transdermal, or subcutaneous administration, but excludes intramuscular administration. "Peripheral" means in a subdermal location, and excludes visceral sites.

"Permeabilizing agent" refers to any naturally occurring or synthetic compound, substance or molecule which has the ability to enhance the permeability of a surface, including but not limited to the skin, the bladder wall, and the like, to a selected compound, such as an API (Active pharmaceutical ingredient).

"Permeation-effective amount" refers to an amount effective to substantially increase the permeability of a surface to a therapeutic agent at a therapeutically effective rate. For intravesical bladder delivery, a permeation-effective amount refers to an amount sufficient to substantially increase the permeability of the bladder wall to a clostridial derivative for a desired time interval without irreversibly damaging the bladder wall, after which time the original selective impermeability of the bladder wall may be restored.

"Pharmaceutical composition" means a composition comprising an active pharmaceutical ingredient, such as, for example, a botulinum toxin, and at least one additional ingredient, such as, for example, a stabilizer or excipient or the like. A pharmaceutical composition is therefore a formulation which is suitable for diagnostic or therapeutic administration to a subject, such as a human patient. The pharmaceutical composition can be, for example, in a lyophilized or vacuum dried condition, a solution formed after reconstitution of the lyophilized or vacuum dried pharmaceutical composition, or as a solution or solid which does not require reconstitution.

The constituent ingredients of a pharmaceutical composition can be included in a single composition (that is, all the constituent ingredients, except for any required reconstitution fluid, are present at the time of initial compounding of the pharmaceutical composition) or as a two-component system, for example a vacuum-dried composition reconstituted with a reconstitution vehicle which can, for example, contain an ingredient not present in the initial compounding of the pharmaceutical composition. A two-component system can provide several benefits, including that of allowing incorporation of ingredients which are not sufficiently compatible for long-term shelf storage with the first component of the two component system. For example, the reconstitution vehicle may include a preservative which provides sufficient protection against microbial growth for the use period, for example one-week of refrigerated storage, but is not present during the two-year freezer storage period during which time it might degrade the toxin. Other ingredients, which may not be compatible with a botulinum toxin or other ingredients for long periods of time, can be incorporated in this manner; that is, added in a second vehicle (e.g. in the reconstitution vehicle) at the approximate time of use. A pharmaceutical composition can also include preservative agents such as benzyl alcohol, benzoic acid, phenol, parabens and sorbic acid. Pharmaceutical compositions can include, for example, excipients, such as surface active agents; dispersing agents; inert diluents; granulating and disintegrating agents; binding agents; lubricating agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; antioxidants; stabilizing agents; and pharmaceutically acceptable polymeric or hydrophobic materials and other ingredients known in the art and described, for example in Genaro, ed., 1985, Remington's Pharmaceutical Sciences, Mack Publishing Co., Easton, Pa., which is incorporated herein by reference.

"Recombinant modified toxin" means a recombinant toxin that shares some or most of the domains with a Botulinum toxin but may or may not target the same cells as native Botulinum neurotoxin.

"Stabilizing", "stabilizes", or "stabilization" means the retention of at least about 20% of the biological activity of an active pharmaceutical ingredient ("API") that has been reconstituted, when compared to the API prior to reconstitution. For example, upon (1) preparation of serial dilutions from a bulk or stock solution, or (2) upon reconstitution of a lyophilized, or vacuum dried botulinum toxin containing pharmaceutical composition which has been stored at or below about −2° C. for between six months and four years, or (3) for an aqueous solution botulinum toxin containing pharmaceutical composition which has been stored at between about 2° C. and about 8° C. for from six months to four years, the botulinum toxin present in the reconstituted or aqueous solution pharmaceutical composition has (in the presence of a compound which is stabilizing, stabilizes or which provides stabilization to the API) greater than about 20% and up to about 100% of the potency or toxicity that the biologically active botulinum toxin had prior to being incorporated into the pharmaceutical composition.

"Stabilizing agent", "stabilization agent" or "stabilizer" means a substance that acts to stabilize an API such that the potency of the pharmaceutical composition is increased relative to an unstabilized composition.

"Stabilizers" can include excipients, and can include protein and non-protein molecules.

"Substantially free" means present at a level of less than one percent by weight of the pharmaceutical composition.

"TEM" as used herein, is synonymous with "Targeted Exocytosis Modulator" or "retargeted endopeptidase." Because of its numerous characteristics, "TEM" will be disclosed in further details at the end of the "Definition" section.

"Therapeutic formulation" means a formulation can be used to treat and thereby alleviate a disorder or a disease, such as, for example, a disorder or a disease characterized by hyperactivity (i.e. spasticity) of a peripheral muscle.

"Therapeutically effective amount" refers to an amount sufficient to achieve a desired therapeutic effect.

"Topical administration" excludes systemic administration of the neurotoxin. In other words, and unlike conventional therapeutic transdermal methods, topical administration of botulinum toxin does not result in significant amounts, such as the majority of, the neurotoxin passing into the circulatory system of the patient.

"Treating" means to alleviate (or to eliminate) at least one symptom of a condition or disorder, such as, for example, wrinkles, spasticity, depression, pain (such as, for example, headache pain), bladder overactivity, or the like, either temporarily or permanently.

"Variant" means a clostridial neurotoxin, such as wild-type botulinum toxin serotype A, B, C, D, E, F or G, that has been modified by the replacement, modification, addition or deletion of at least one amino acid relative to wild-type botulinum toxin, which is recognized by a target cell, internalized by the target cell, and catalytically cleaves a SNARE (SNAP (Soluble NSF Attachment Protein) Receptor) protein in the target cell.

An example of a variant neurotoxin component can comprise a variant light chain of a botulinum toxin having one or more amino acids substituted, modified, deleted and/or added. This variant light chain may have the same or better ability to prevent exocytosis, for example, the release of neurotransmitter vesicles. Additionally, the biological effect of a variant may be decreased compared to the parent chemical entity. For example, a variant light chain of a botulinum toxin type A having an amino acid sequence removed may have a shorter biological persistence than that of the parent (or native) botulinum toxin type A light chain.

"Vehicle" or "reconstitution vehicle" means a liquid composition that can be used to reconstitute a solid botulinum formulation into a liquid botulinum pharmaceutical composition.

"Wild type neuronal binding moiety" means that portion of a neurotoxin which is native to the neurotoxin and which exhibits a specific binding affinity for a receptor on a neuron. Thus, wild type or native neuronal binding moiety excludes a binding moiety with is not native to the neurotoxin.

TEMs

Generally, a TEM comprises an enzymatic domain from a Clostridial toxin light chain, a translocation domain from a Clostridial toxin heavy chain, and a targeting domain. The targeting domain of a TEM provides an altered cell targeting capability that targets the molecule to a receptor other than the native Clostridial toxin receptor utilized by a naturally-occurring Clostridial toxin. This re-targeted capability is achieved by replacing the naturally-occurring binding domain of a Clostridial toxin with a targeting domain having a binding activity for a non-Clostridial toxin receptor. Although binding to a non-Clostridial toxin receptor, a TEM undergoes all the other steps of the intoxication process including internalization of the TEM/receptor complex into the cytoplasm, formation of the pore in the vesicle membrane and di-chain molecule, translocation of the enzymatic domain into the cytoplasm, and exerting a proteolytic effect on a component of the SNARE complex of the target cell.

As used herein, the term "Clostridial toxin enzymatic domain" refers to a Clostridial toxin polypeptide located in the light chain of a Clostridial toxin that executes the enzymatic target modification step of the intoxication process. A Clostridial toxin enzymatic domain includes a metalloprotease region containing a zinc-dependent endopeptidase activity which specifically targets core components of the neurotransmitter release apparatus. Thus, a Clostridial toxin enzymatic domain specifically targets and proteolytically cleavages of a Clostridial toxin substrate, such as, e.g., SNARE proteins like a SNAP-25 substrate, a VAMP substrate and a Syntaxin substrate.

A Clostridial toxin enzymatic domain includes, without limitation, naturally occurring Clostridial toxin enzymatic domain variants, such as, e.g., Clostridial toxin enzymatic domain isoforms and Clostridial toxin enzymatic domain subtypes; non-naturally occurring Clostridial toxin enzymatic domain variants, such as, e.g., conservative Clostridial toxin enzymatic domain variants, non-conservative Clostridial toxin enzymatic domain variants, Clostridial toxin enzymatic domain chimeras, active Clostridial toxin enzymatic domain fragments thereof, or any combination thereof. Non-limiting examples of a Clostridial toxin enzymatic domain include, e.g., a BoNT/A enzymatic domain, a BoNT/B enzymatic domain, a BoNT/C1 enzymatic domain, a BoNT/D enzymatic domain, a BoNT/E enzymatic domain, a BoNT/F enzymatic domain, a BoNT/G enzymatic domain, a TeNT enzymatic domain, a BaNT enzymatic domain, and a BuNT enzymatic domain.

As used herein, the term "Clostridial toxin translocation domain" refers to a Clostridial toxin polypeptide located within the amino-terminal half of the heavy chain of a Clostridial toxin that executes the translocation step of the intoxication process. The translocation step appears to involve an allosteric conformational change of the translocation domain caused by a decrease in pH within the intracellular vesicle. This conformational change results in the formation of a pore in the vesicular membrane that permits the movement of the light chain from within the vesicle into the cytoplasm. Thus, a Clostridial toxin translocation domain facilitates the movement of a Clostridial toxin light chain across a membrane of an intracellular vesicle into the cytoplasm of a cell.

A Clostridial toxin translocation domain includes, without limitation, naturally occurring Clostridial toxin translocation domain variants, such as, e.g., Clostridial toxin translocation domain isoforms and Clostridial toxin translocation domain subtypes; non-naturally occurring Clostridial toxin translocation domain variants, such as, e.g., conservative Clostridial toxin translocation domain variants, non-conservative Clostridial toxin translocation domain variants, Clostridial toxin translocation domain chimerics, active Clostridial toxin translocation domain fragments thereof, or any combination thereof. Non-limiting examples of a Clostridial toxin translocation domain include, e.g., a BoNT/A translocation domain, a BoNT/B translocation domain, a BoNT/C1 translocation domain, a BoNT/D translocation domain, a BoNT/E translocation domain, a BoNT/F translocation domain, a BoNT/G translocation domain, a TeNT translocation domain, a BaNT translocation domain, and a BuNT translocation domain.

As used herein, the term "targeting domain" is synonymous with "binding domain" or "targeting moiety" and refers to a peptide or polypeptide that executes the receptor binding and/or complex internalization steps of the intoxication process, with the proviso that the binding domain is not identical to a Clostridial toxin binding domain found within the carboxyl-terminal half of the heavy chain of a Clostridial toxin. A targeting domain includes a receptor binding region that confers the binding activity and/or specificity of the targeting domain for its cognate receptor. As used herein, the term "cognate receptor" refers to a receptor for which the targeting domain preferentially interacts with under physiological conditions, or under in vitro conditions substantially approximating physiological conditions. As used herein, the term "preferentially interacts" is synonymous with "preferentially binding" and refers to an interaction that is statistically significantly greater in degree relative to a control. With reference to a targeting domain disclosed herein, a targeting domain binds to its cognate receptor to a statistically significantly greater degree relative to a non-cognate receptor. Said another way, there is a discriminatory binding of the targeting domain to its cognate receptor relative to a non-cognate receptor. Thus, a targeting domain directs binding to a TEM-specific receptor located on the plasma membrane surface of a target cell.

A targeting domain disclosed herein may be one that preferentially interacts with a receptor located on a sensory neuron. In another embodiment, a targeting domain disclosed herein may be one that preferentially interacts with a receptor located on a sympathetic neuron, or a parasympathetic neuron.

In another embodiment, a targeting domain disclosed herein is an opioid peptide targeting domain, a galanin peptide targeting domain, a PAR peptide targeting domain, a somatostatin peptide targeting domain, a neurotensin peptide targeting domain, a SLURP peptide targeting domain, an angiotensin peptide targeting domain, a tachykinin peptide targeting domain, a Neuropeptide Y related peptide targeting domain, a kinin peptide targeting domain, a melanocortin peptide targeting domain, or a granin peptide targeting domain, a glucagon like hormone peptide targeting domain, a secretin peptide targeting domain, a pituitary adenylate cyclase activating peptide (PACAP) peptide targeting domain, a growth hormone-releasing hormone (GHRH) peptide targeting domain, a vasoactive intestinal peptide (VIP) peptide targeting domain, a gastric inhibitory peptide (GIP) peptide targeting domain, a calcitonin peptide targeting domain, a visceral gut peptide targeting domain, a neurotrophin peptide targeting domain, a head activator (HA) peptide, a glial cell line-derived neurotrophic factor (GDNF) family of ligands (GFL) peptide targeting domain, a RF-amide related peptide (RFRP) peptide targeting domain, a neurohormone peptide targeting domain, or a neuroregulatory cytokine peptide targeting domain, an interleukin (IL) targeting domain, vascular endothelial growth factor (VEGF) targeting domain, an insulin-like growth factor (IGF) targeting domain, an epidermal growth factor (EGF) targeting domain, a Transformation Growth Factor-β (TGFβ) targeting domain, a Bone Morphogenetic Protein (BMP) targeting domain, a Growth and Differentiation Factor (GDF) targeting domain, an activin targeting domain, or a Fibroblast Growth Factor (FGF) targeting domain, or a Platelet-Derived Growth Factor (PDGF) targeting domain.

An opioid peptide targeting domain may include an enkephalin peptide, a bovine adrenomedullary-22 (BAM22) peptide, an endomorphin peptide, an endorphin peptide, a dynorphin peptide, a nociceptin peptide, or a hemorphin peptide.

Thus, a TEM can comprise a targeting domain in any and all locations with the proviso that TEM is capable of performing the intoxication process. Non-limiting examples include, locating a targeting domain at the amino terminus of a TEM; locating a targeting domain between a Clostridial toxin enzymatic domain and a Clostridial toxin translocation domain of a TEM; and locating a targeting domain at the carboxyl terminus of a TEM. Other non-limiting examples include, locating a targeting domain between a Clostridial toxin enzymatic domain and a Clostridial toxin translocation domain of a TEM. The enzymatic domain of naturally-occurring Clostridial toxins contains the native start methionine. Thus, in domain organizations where the enzymatic domain is not in the amino-terminal location an amino acid sequence comprising the start methionine should be placed in front of the amino-terminal domain. Likewise, where a targeting domain is in the amino-terminal position, an amino acid sequence comprising a start methionine and a protease cleavage site may be operably-linked in situations in which a targeting domain requires a free amino terminus, see, e.g., Shengwen Li et al., Degradable Clostridial Toxins, U.S. patent application Ser. No. 11/572,512 (Jan. 23, 2007), which is hereby incorporated by reference in its entirety. In addition, it is known in the art that when adding a polypeptide that is operably-linked to the amino terminus of another polypeptide comprising the start methionine that the original methionine residue can be deleted.

A TEM disclosed herein may optionally comprise an exogenous protease cleavage site that allows the use of an exogenous protease to convert the single-chain polypeptide form of a TEM into its more active di-chain form. As used herein, the term "exogenous protease cleavage site" is synonymous with a "non-naturally occurring protease cleavage site" or "non-native protease cleavage site" and means a protease cleavage site that is not naturally found in a di-chain loop region from a naturally occurring Clostridial toxin.

Although TEMs vary in their overall molecular weight because the size of the targeting domain, the activation process and its reliance on an exogenous cleavage site is essentially the same as that for recombinantly-produced Clostridial toxins. See e.g., Steward, et al., Activatable Clostridial Toxins, US 2009/0081730; Steward, et al., Modified Clostridial Toxins with Enhanced Translocation Capabilities and Altered Targeting Activity For Non-Clostridial Toxin Target Cells, U.S. patent application Ser. No. 11/776, 075; Steward, et al., Modified Clostridial Toxins with Enhanced Translocation Capabilities and Altered Targeting Activity for Clostridial Toxin Target Cells, US 2008/0241881; Steward, et al., Degradable Clostridial Toxins, US 2011/0287517, each of which is hereby incorporated by reference. In general, the activation process that converts the single-chain polypeptide into its di-chain form using exogenous proteases can be used to process TEMs having a targeting domain organized in an amino presentation, central presentation, or carboxyl presentation arrangement. This is because for most targeting domains the amino-terminus of the moiety does not participate in receptor binding. As such, a wide range of protease cleavage sites can be used to produce an active di-chain form of a TEM. However, targeting domains requiring a free amino-terminus for receptor binding require a protease cleavage site whose scissile bond is located at the carboxyl terminus. The use of protease cleavage site in the design of a TEM are described in, e.g., Steward, et al., Activatable Clostridial toxins, US 2009/0069238; Ghanshani, et al., Modified Clostridial Toxins Comprising an Integrated Protease Cleavage Site-Binding Domain, US 2011/0189162; and Ghanshani, et al., Methods of Intracellular Conversion of Single-Chain Proteins into their Di-chain Form, International Patent Application Serial No. PCT/US2011/22272, each of which is incorporated by reference in its entirety.

Pharmaceutical Compositions

Aspects of the present disclosure provide, in part, a pharmaceutical composition suitable for intravesical bladder delivery, comprising a clostridial derivative and at least one permeabilizing agent.

Clostridial Derivative:

A clostridial derivative as defined herein encompasses native or recombinant neurotoxins, recombinant modified toxins, fragments thereof, a Targeted vesicular Exocytosis Modulator (TEM), or combinations thereof. In some embodiments, tihe clostridial derivative is a native or modified botulinum toxin. In one embodiment, the clostridial derivative is a botulinum toxin type A. In some embodiments, the clostridial derivative is a botulinum type B, $C_1$, D, E or F. In alternative embodiments, the clostridial derivative comprises a TEM.

In some embodiments, the present pharmaceutical composition comprises a therapeutically effective amount of the clostridial derivative. A therapeutically effective amount refers to the total amount of the clostridial derivative administered to an individual in one setting. As such, an effective amount of a Clostridial derivative and/or TEM does not refer to the amount administered per site. For example, an effective amount of a Clostridial toxin, such as a botulinum toxin, administered to an individual may be 10 U, whereas the amount of toxin administered per site may be 2 U, i.e., 2 U at five different sites. In some embodiments, the therapeutically effective amount of the botulinum toxin ranges from 10 U to 1000 U, more preferably from about 50 U to about 500 U.

With reference to a combination therapy comprising a Clostridial toxin and a TEM, an effective amount of a Clostridial toxin is one where in combination with a TEM the amount of the Clostridial toxin achieves the desired therapeutic effect, but such an amount administered on its own would be ineffective. For example, typically about 75-125 U of BOTOX® (Allergan, Inc., Irvine, Calif.), a BoNT/A, is administered by intramuscular injection per muscle undergoing dystonic spasms in order to treat cervical dystonia. In combination therapy, a suboptimal effective amount of BoNT/A would be administered to treat cervical dystonia when such toxin is used in a combined therapy with a TEM.

Permeabilizing Agents

Examples of permeabilizing agents include but are not limited to anionic surfactants, cationic surfactants, nonionic surfactants, glycols, chelators, cationic polymers, mucoadhesives, polypeptides, or mixtures thereof.

In some embodiments, the permeabilizing agent selectively binds to the clostridial derivative, such as a botulinum toxin, to form a complex. In alternative embodiments, the permeabilizing agent does not bind to the botulinum toxin. In alternative embodiments, the permeabilizing agent interacts with the clostridial derivative through Van der Wall interactions.

In certain embodiments, the permeabilizing agent can be anionic surfactants. Examples of anionic surfactants suitable for the present formulation include but are not limited to SDS, sodium lauryl sulfate, their analogs, derivatives or any combinations thereof.

In certain embodiments, the permeabilizing agent can be cationic surfactants. Examples of cationic surfactants suitable for the present formulation include but are not limited to Protamine sulfate, benzalkonium bromide, quaternary ammonium salts such as poly (dimethylimino)-2-butene-1, 4-diyl chloride, α-[4-tris(2-hydroxyethyl) ammonium-2-butenyl-ω-tris (2-hydroxyethyl) ammonium]-dichloride (chemical registry number 75345-27-6) generally available as polyquaternium 1® from ONYX Corporation, benzalkonium halides, and biguanides such as salts of alexidine, alexidine free base, salts of chlorhexidine, hexamethylene biguanides and their polymers, analogs and derivatives. The salts of alexidine and chlorhexidine can be either organic or inorganic and are typically nitrates, acetates, phosphates, sulfates, halides and the like, or any combination thereof, and the like.

In certain embodiments, the permeabilizing agent can be other cationic agents, including but not limited to poly (ethylenimine) (PEI), Olevlamine, dioleyl-phosphatidylethanolamine (DOPE) and dioleoyl trimethylammonium-propane (DOTAP), their analogs, derivatives, or combinations thereof.

In certain embodiments, the permeabilizing agent can comprise polyethylene glycol (PEG) or polyethylene oxide (PEO). The PEG can comprise, for example, PEG with a molecular mass ranging from about 200 grams per mole (g/m) to about 20,000 grams per mole (g/m). In one embodiment, the permeabilizing agent comprises Polyethylene glycol 3350.

In certain embodiments the permeabilizing agent can comprise a poloxamer. The poloxamer can comprise, for example, P80, P124, P188, P237, P338, and P407, their analogs, derivatives or combinations thereof. In certain embodiments the permeabilizing agent can comprise a povidone (PVP). The PVP can comprise, for example, PVP polymers, and analogs or derivatives.

In certain embodiments, the permeabilizing agent can comprise L or D polypeptides, of molecular weight ranging from about 1000 to about 100000 daltons. In one embodiment, the permeabilizing agent is Poly-L-lysine. In another embodiment, the permeabilizing agent includes cell-penetrating peptides.

In certain embodiments, the permeabilizing agent can comprise benzyl alcohol and the like, Polyhexamethylene Biguanide (high and/or low molecular weight) and the like, proteins including but not limited native or recombinant human sera albumin, polymyxin B and the like, or mixtures thereof.

In certain embodiments, the permeabilizing agent includes nonionic surfactants. Examples of nonionic surfactants suitable for the present formulation include but are not limited to alkyl aryl polyethers and analogs, derivatives thereof (e.g TX-100, analogs or derivatives), poloxamers, polyoxyethylene ethers (e.g. Brij families), Tween, Big CHAPS, Deoxy Big CHAPS, Tyloxapol, Sorbitan monooleate (SPAN) 20, 40, 60, Cremophor EL, Alpha-Tocopherol TPGS, Polyoxyl stearate 40, analogs and derivatives, or combinations thereof.

In some embodiments, the permeabilizing agent comprises an alkyl aryl polyether, analogs or derivatives. In one embodiment, the permeabilizing agent comprises octyl phenol ethoxylate, analogs or derivatives Octyl phenol ethoxylate is also known as polyoxyethylene octyl phenyl ether, 4-octylphenol polyethoxylate, Mono 30, TX-100, t-octyl-phenoxypolyethoxyethanol, octoxynol-9, or the more commonly known tradename of Triton™ X-100. In alternative embodiments, the permeabilizing agent comprises Nonoxynol 9, analogs, or derivatives.

In certain embodiments, the permeabilizing agent comprises a cationic polymer. In some embodiments, the cationic polymer is a mucoadhesive. In some embodiments, the cationic polymer includes chitosan, chondroitin, chitosan analogs, chondroitin analogs, chitosan derivatives, or chondroitin derivatives.

In some embodiments, the present pharmaceutical composition comprises a clostridial derivative and at least one permeabilizing agent. In one embodiment, the clostridial derivative is a botulinum toxin. In one embodiment, the clostridial derivative includes a botulinum toxin. In some embodiments, the at least one permeabilizing agent comprises chitosan, chitosan analog or chitosan derivative and TX-100, TX-100 analogs or TX-100 derivatives. In some embodiments, the present pharmaceutical composition comprises a botulinum toxin, chitosan, chitosan analog or chitosan derivative and nonoxynol-9, nonoxynol-9 analogs or nonoxynol-9 derivatives. In alternative embodiments, the clostridial derivative is a TEM In alternative embodiments, the formulation comprises a botulinum toxin and a TEM.

In certain embodiments, the permeabilizing agent can comprise chelators, including but not limited to EDTA, EGTA (ethylene glycol tetraacetic acid), cyclohexanediamine tetraacetate (CDTA), hydroxyethylethylenediamine triacetate (HEDTA), diethylenetriamine pentaacetate (DTPA), 1,2-diaminocyclohexane tetraacetate, and hexametaphosphate. These agents preferably are employed as salts, typically sodium salts such as disodium EDTA, trisodium HEDTA, sodium hexametaphosphate, or any combinations thereof, and the like.

Thus, in one aspect, the present pharmaceutical composition comprises a clostridial derivative, and at least one permeabilizing agent, wherein the pharmaceutical formulation is suitable for intravesical bladder delivery. In some embodiments, the clostridial derivative comprises a botulinum toxin and the permeabilizing agent comprises a mucoadhesive and a surfactant. In some embodiments, the mucoadhesive includes chitosan, chitosan analogs, chitosan derivatives, chondroitin, chondroitin analogs and chondroitin derivatives. In some embodiments, the surfactant includes nonionic surfactants. In one embodiment, the present pharmaceutical composition comprises a botulinum toxin type A, chitosan, chitosan analogs or chitosan derivatives and TX-100, TX-100 analogs or TX-100 derivatives. In some embodiments, the surfactant comprises nonoxynol-9, nonoxynol-9 analogs or nonoxynol-9 derivatives. In alternative embodiments, the clostridial derivative is a TEM.

In some embodiments, the permeabilizing agent is present in a permeation-effective amount. In one embodiment, a permeation effective amount refers to an amount effective to substantially increase the permeability of the bladder wall surface with limited damage to the bladder integrity. In one embodiment, the permeation-effective amount refers to an amount effective to allow permeation of a therapeutically effective amount of a botulinum neurotoxin through the bladder wall at a therapeutically effective rate. In one embodiment, the permeation effective amount refers to an amount effective to substantially increase the permeability of the bladder wall surface for a desired time interval to a therapeutically effective amount of the toxin at a therapeutically effective rate without irreversibly damaging the bladder wall. In some embodiments, the increased permeability is reversible after a desired time interval, after which the bladder wall may fully or partially restore its original impermeability or selective permeability. In some embodiments, the bladder wall restores its original impermeability or selective permeability after a time interval ranging from about 1 hour to about 24 hours after intravesical instillation. In some embodiments, the time interval ranges from about 3 hours to about 18 hours. In some embodiments, the time interval ranges from about 4 hours to about 12 hours. The recovery rate whereby the bladder wall restores its original selective permeability or impermeability can be influenced by the characteristics of the permeabilizing agent selected, the amount, and the characteristics of the permeation surface, the exposure time and the environment surrounding the permeation surface. In one embodiment, the bladder integrity following administration of the present pharmaceutical composition can be evaluated by the extent of immune response, such as the presence of specific immune cells.

The permeation-effective amount varies depending on several factors, including but not limited to the characteristics of the clostridial derivative, the characteristics of the permeation surface (e.g. the bladder wall), the type of permeabilizing agent, and the environment surrounding the permeation surface.

In some embodiments, the permeation-effective amount of the permeabilizing agent ranges from about 0.005% to about 10% (w/v), more preferably from about 0.025% to about 5% (w/v), and most preferably from about 0.05% to about 0.5% (w/v). In some embodiments, the present pharmaceutical formulation comprises a permeation-effective amount of Triton™ X-100, Triton™ X-100 analogs or derivatives from 0.005% to about 10% (w/v), more preferably from about 0.025% to about 5% (w/v), and most preferably from about 0.1% to about 0.5% (w/v). In one specific embodiment, the permeative effective amount of Triton™ X-100 is about 0.1% (w/v).

In some embodiments, the permeabilizing agent is used in combination with a mucoadhesive. In some embodiments, the mucoadhesive is a cationic polymer. In some embodiments, the mucoadhesive includes chitosan, chitosan analogs, chitosan derivatives, chondroitin, chondroitin analogs or chondroitin derivatives. In some embodiments, the permeation-effective amount of the mucoadhesive ranges from about 0.005% to 10% (w/v), more preferably from about 0.02% to about 5% (w/v), and most preferably from about 0.05% to about 2% (w/v). In one embodiment, the permeation-effective amount of chitosan, chitosan analogs or chitosan derivatives is about 1% (w/v). In some embodiments, the formulation comprises: (1) a botulinum toxin, (2) Triton™ X-100, Triton™ X-100 analog, Triton™X-100 derivatives or mixtures thereof; and (3) chitosan, chitosan analogs, chitosan derivatives, or mixtures thereof. In some embodiments, the formulation comprises: (1) a botulinum toxin type A, (2) Triton™X-100, Triton™X-100 analogs, Triton™X-100 derivatives, or mixtures thereof; and (3) chitosan, chitosan analogs, chitosan derivatives, or mixtures thereof. In some embodiments, the formulation comprises about 20 units to about 300 units of botulinum toxin type A, about 0.5% to about 2% (w/v) chitosan, chitosan analogs, derivatives; or mixtures thereof, and about 0.05% to about 1% (w/v) Triton™ X-100, analogs, derivatives or mixtures thereof. In one embodiment, the formulation comprises from about 100 or 200 units of botulinum toxin type A, about 1% chitosan and about 0.1% (w/v) Triton™ X-100.

In some embodiments, the permeabilizing agent is Nonoxynol 9. In some embodiments, the permeation-effective amount of Nonoxynol 9 ranges from about 0.005% to about 10% (w/v), more preferably from about 0.025% to about 5% (w/v), and most preferably from about 0.05% to about 0.5% (w/v). In one specific embodiment, the present pharmaceutical formulation comprises a permeation-effective amount of Nonoxynol 9 of about 0.1% (w/v). In one specific embodiment, the present pharmaceutical formulation comprises a permeation-effective amount of Nonoxynol 9 of about 0.5% (w/v). In some embodiments, nonoxynol 9 is used in combination with a mucoadhesive. In some embodiments, the mucoadhesive includes chitosan, chitosan analogs, chitosan derivatives, chondroitin, chondroitin analogs or chondroitin derivatives. In some embodiments, the permeation-effective amount of the mucoadhesive ranges from about 0.005% to 10% (w/v), more preferably from about 0.02% to about 5% (w/v), and most preferably from about 0.1% to about 2% (w/v). In some embodiments, the permeation-effective amount of chitosan or chitosan derivatives range from about 0.005% to 10% (w/v), more preferably from about 0.02% to about 5% (w/v), and most preferably from about 0.1% to about 2% (w/v). In one embodiment, the permeation-effective amount of chitosan or chitosan derivatives is about 1% (w/v).

In some embodiments, the permeabilizing agent can comprise recombinant or native human serum albumin.

In some embodiments, the present composition does not comprise any animal-derived proteins. In one embodiment, the present composition comprises a botulinum toxin, a TEM, or a recombinant modified toxin (as the active ingredient) and a suitable polysaccharide, or non-protein excipient as a stabilizer or excipient.

Thus, aspects of the present disclosure provide a pharmaceutical composition comprising a clostridial derivative and one or more permeabilizing agents, wherein the pharmaceutical composition is suitable for intravesical bladder delivery and wherein the one or more permeabilizing agent is present in a permeation-effective amount, as disclosed herein. Embodiments of the present composition include therapeutic agents and/or excipients that will either cause or enhance the pharmacological effects of the clostridial derivatives.

Excipients can also be added to increase the stability of the formulation, increase the action of permeabilizing agents (example EDTA or other chelating agents) or to increase the retention of the formulation through increased viscoelastic properties that will occur immediately (example: carboxymethyl cellulose (CMC), hydroxypropyl cellulose (HPMC), alginate) or upon change in temperature (example: poloxamer 407), pH (Carbopol P-934, P940) and/or ionic (example: Gelrite gellan gum, alginate) environments.

Excipients can also be added to modulate the tonicity and/or pH of urine and skin to increase delivery, stability, bioavailability and/or therapeutic activity of formulations.

In another aspect, the present disclosure provides a method for making a pharmaceutical formulation for suitable for intravesical bladder administration, the method comprising providing a solution comprising at least one permeabilizing agent as disclosed herein, adding the solution to a composition comprising a clostridial derivative as disclosed herein. In some embodiments, the method comprises adding from about 50 ml to about 100 ml of the solution to the composition comprising the clostridial derivative. In some embodiments, the clostridial derivative is a botulinum toxin. In one embodiment, the method comprises adding about 50 ml to about 100 ml of an aqueous solution comprising about 1% (w/v) chitosan, analogs or derivatives and about 0.1% (w/v) Triton™X-100, analogs or derivatives, to a botulinum toxin type A. In one embodiment, the method comprises adding a 50 ml aqueous solution comprising about 1% (w/v) chitosan and about 0.1% (w/v) Triton™X-100 to a vial containing about 100 Units or 200 Units of a lyophilized botulinum toxin type A; and mixing gently to rehydrate the lyophilized botulinum toxin type A.

In some embodiments, excipients can also be added to act as carriers of the clostridial derivative. In one embodiment, poly-L-lysine is added as a carrier.

A composition disclosed herein is generally administered as a pharmaceutical acceptable composition. As used herein, the term "pharmaceutically acceptable" means any molecular entity or composition that does not produce an adverse, allergic or other untoward or unwanted reaction when administered to an individual. As used herein, the term "pharmaceutically acceptable composition" is synonymous with "pharmaceutical composition" and means a therapeutically effective concentration of an active ingredient, such as, e.g., any of the Clostridial toxins and/or TEMs disclosed herein. A pharmaceutical composition disclosed herein is useful for medical and veterinary applications. A pharmaceutical composition may be administered to an individual alone, or in combination with other supplementary active ingredients, agents, drugs or hormones. The pharmaceutical compositions may be manufactured using any of a variety of processes, including, without limitation, conventional mixing, dissolving, granulating, dragee-making, levigating, emulsifying, encapsulating, entrapping, and lyophilizing. The pharmaceutical composition can take any of a variety of forms including, without limitation, a sterile solution, suspension, emulsion, lyophilizate, tablet, pill, pellet, capsule, powder, syrup, elixir or any other dosage form suitable for administration.

The present pharmaceutical composition may optionally include a pharmaceutically acceptable carrier that facilitates processing of an active ingredient into pharmaceutically acceptable compositions. As used herein, the term "pharmacologically acceptable carrier" is synonymous with "pharmacological carrier" and means any carrier that has substantially no long term or permanent detrimental effect when administered and encompasses terms such as "pharmacologically acceptable vehicle, stabilizer, diluent, additive, auxiliary or excipient." Such a carrier generally is mixed with an active compound, or permitted to dilute or enclose the active compound and can be a solid, semi-solid, or liquid agent. It is understood that the active ingredients can be soluble or can be delivered as a suspension in the desired carrier or diluent. Any of a variety of pharmaceutically acceptable carriers can be used including, without limitation, aqueous media such as, e.g., water, saline, glycine, hyaluronic acid and the like; solid carriers such as, e.g., mannitol, lactose, starch, magnesium stearate, sodium saccharin, talcum, cellulose, glucose, sucrose, magnesium carbonate, and the like; solvents; dispersion media; coatings; antibacterial and antifungal agents; isotonic and absorption delaying agents; or any other inactive ingredient. Selection of a pharmacologically acceptable carrier can depend on the mode of administration. Except insofar as any pharmacologically acceptable carrier is incompatible with the active ingredient, its use in pharmaceutically acceptable compositions is contemplated. Non-limiting examples of specific uses of such pharmaceutical carriers can be found in PHARMACEUTICAL DOSAGE FORMS AND DRUG DELIVERY SYSTEMS (Howard C. Ansel et al., eds., Lippincott Williams & Wilkins Publishers, 7th ed. 1999); REMINGTON: THE SCIENCE AND PRACTICE OF PHARMACY (Alfonso R. Gennaro ed., Lippincott, Williams & Wilkins, 20th ed. 2000); GOODMAN & GILMAN'S THE PHARMACOLOGICAL BASIS OF THERAPEUTICS (Joel G. Hardman et al., eds., McGraw-Hill Professional, 10th ed. 2001); and HANDBOOK OF PHARMACEUTICAL EXCIPIENTS (Raymond C. Rowe et al., APhA Publications, 4th edition 2003). These protocols are routine procedures and any modifications are well within the scope of one skilled in the art and from the teaching herein.

A pharmaceutical composition disclosed herein can optionally include, without limitation, other pharmaceutically acceptable components (or pharmaceutical components), including, without limitation, buffers, preservatives, tonicity adjusters, salts, antioxidants, osmolality adjusting agents, physiological substances, pharmacological substances, bulking agents, emulsifying agents, wetting agents, sweetening or flavoring agents, and the like. Various buffers and means for adjusting pH can be used to prepare a pharmaceutical composition disclosed herein, provided that the resulting preparation is pharmaceutically acceptable. Such buffers include, without limitation, acetate buffers, citrate buffers, phosphate buffers, neutral buffered saline, phosphate buffered saline and borate buffers. It is understood that acids or bases can be used to adjust the pH of a composition as needed. Pharmaceutically acceptable antioxidants include, without limitation, sodium metabisulfite, sodium thiosulfate, acetylcysteine, butylated hydroxyanisole and butylated hydroxytoluene. Useful preservatives include, without limitation, benzalkonium chloride, chlorobutanol, thimerosal, phenylmercuric acetate, phenylmercuric nitrate, a stabilized oxy chloro composition and chelants, such as, e.g., DTPA or DTPA-bisamide, calcium DTPA, and CaNaDTPA-bisamide. Tonicity adjustors useful in a pharmaceutical composition include, without limitation, salts such as, e.g., sodium chloride, potassium chloride, mannitol or glycerin and other pharmaceutically acceptable tonicity adjustor. The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. It is understood that these and other substances known in the art of pharmacology can be included in a pharmaceutical composition. Exemplary pharmaceutical composition comprising a Clostridial toxin and a TEM are described in Hunt, et al., Animal Protein-Free Pharmaceutical Compositions, U.S. Ser. No. 12/331,816; and Dasari, et al., Clostridial Toxin Pharmaceutical Compositions, WO/2010/090677, each of which is hereby incorporated by reference in its entirety.

The choice of suitable pharmaceutically acceptable carriers will depend on the exact nature of the particular formulation desired, e.g., whether the present composition is to be formulated into a liquid solution, a lyophilized powder to be reconstituted upon use, a suspension solution, nanoparticles, liposomes or microemulsions.

The choice of a suitable pharmaceutically acceptable carrier will also depend on the route of administration. Preferably, the carrier is formulated to be suitable for a chosen route of administration. Administration modes of the present pharmaceutical formulation include but are not limited to injection, needle-free injections (e.g. Bioject, JetTouch), electromotive, transdermal delivery or intravesical instillation. In one specific embodiment, the formulation comprises a pharmaceutical acceptable carrier for bladder instillation. In one embodiment, the pharmaceutical carrier comprises poly lysine.

Methods of Treatment

Aspects of the present disclosure provide, in part, a method of treating medical conditions using a pharmaceutical composition comprising a clostridial derivative and at least one permeabilizing agent, wherein administration of the present pharmaceutical composition prevents or reduces a symptom associated with the medical condition being treated. In some embodiments, the administration is by injection. In alternative embodiments, the administration is transdermal, subcutaneous, or topical. In yet alternative embodiments, the administration is by intravesical delivery.

In some embodiments, the present disclosure provides methods of treating diseases, disorders, conditions, and the like, comprising the step of administering a pharmaceutical formulation of the present disclosure to a subject in need thereof in an amount sufficient to produce improved patient function. In certain embodiments, the diseases are of a neuromuscular nature, such as, for example, those diseases that affect muscles and nerve control thereof, such as, for example, overactive bladder, and the like. Certain embodiments relate to the treatment of pain, such as, for example, treatment of headache pain, or back pain, or muscle pain, or the like. In certain embodiments, methods of the invention encompass the treatment of psychological disorders, including, for example, depression, anxiety, and the like.

Treatment of Urological Disorders

In some embodiments, the medical disorder comprises urological bladder diseases and conditions, including but not limited to overactive bladder (OAB), cystitis, bladder cancer, neurogenic detrusor overactivity (NDO). In an embodiment, the present disclosure also provides methods for treating a patient suffering from overactive bladder (OAB), such as, for example, that due to a neurologic condition (NOAB), or idiopathic OAB (IOAB).

Neurogenic bladder dysfunction is a dysfunction that results from interference with the normal nerve pathways associated with urination. One type of neurogenic bladder dysfunction is overactive (spastic or hyper-reflexive) bladder. An overactive neurogenic bladder is characterized by uncontrolled, frequent expulsion of urine from the bladder. There may be reduced bladder capacity and incomplete emptying of urine. Spastic bladder may be caused by an inability of the detrusor muscle of the bladder to inhibit emptying contractions until a reasonable amount of urine has accumulated. Often, a strong urge to void is experienced when only a small amount of urine is in the bladder. The patient may report symptoms of urgency, frequency, nocturia, and incontinence. Another type of neurogenic bladder dysfunction is characterized by difficulty in relaxing the urinary sphincter muscle. The sphincter may be spastic. This causes difficulty in emptying the bladder, which can lead to urinary retention and urinary tract infections. In another type of neurogenic bladder dysfunction, both the detrusor muscle and the urinary sphincter simultaneously contract resulting in urinary retention. A dysfunction associated with simultaneous contraction of both the detrusor and the urinary sphincter is called detrusor-external sphincter dyssynergia (DESD) U.S. Pat. Nos. 7,449,192; 8,062,807 and 7,968,104, each of which is hereby incorporated by reference in its entirety, disclose methods for treating a patient with a neurogenic bladder dysfunction by injecting a therapeutically effective amount of a botulinum toxin, into the bladder wall of the patient.

Interstitial cystitis (IC) is an incurable, chronic, debilitating disease of the urinary bladder that is characterized by bladder pain, chronic pelvic pain, irritative voiding symptoms and sterile urine. In IC, the bladder wall typically shows inflammatory infiltration with mucosal ulceration and scarring which causes smooth muscle contraction, diminished urinary capacity, hematuria and frequent, painful urination.

In some embodiments, pharmaceutical formulations of the present disclosure can be administered to the bladder or its vicinity, e.g. the detrusor, wherein the administration of the formulation reduces the urge incontinence associated with overactive bladder. In certain embodiments, the dosage can range from about 10 Units to about 200 U per treatment. In some embodiments, the present pharmaceutical formulations can be administered by intravesical bladder delivery.

Thus, aspects of the present disclosure further provide for a method for treating a bladder condition in a patient in need thereof, comprising: providing a pharmaceutical composition as disclosed herein, comprising a clostridial derivative, and at least one permeabilizing agent, wherein the permeabilizing agent is present in an amount effective to substantially enhance the permeability of the bladder wall to the clostridial derivative, at a therapeutically effective rate, and without irreversibly damaging the bladder wall; and instilling the pharmaceutically composition to the bladder via a catheter; thereby treating the bladder conditions. In one embodiment, the method further comprises pre-treating the bladder wall with the pharmaceutical composition prior to the step of instilling.

In some embodiments, the method for treating a bladder condition in a patient comprising providing a solution comprising a permeabilizing agent; adding the solution to a clostridial derivative to form a therapeutic formulation, instilling the therapeutic formulation through a catheter into a patient's bladder. In some embodiments, the clostridial derivative is a botulinum toxin. In alternative embodiments, the clostridial derivative is a TEM. In one embodiment, the clostridial derivative is a botulinum toxin type A. In some embodiments, the permeabilizing agent is a surfactant. In one embodiment, the permeabilizing agent is a nonionic surfactant. In some embodiments, the permeabilizing agent further comprises a cationic polymer. In some embodiments, the cationic polymer is a bioadhesive or mucoadhesive. In some embodiment, the mucoadhesive comprises a chitosan, chitosan analog or derivative. In some embodiments, the method comprises mixing a solution comprising a nonionic surfactant and a cationic polymer to a botulinum toxin.

In another aspect, the present disclosure provides a method for alleviating the symptoms of Interstitial cystitis (IC) in a patient, the method comprising: providing a pharmaceutical composition, comprising a clostridial derivative and at least one permeabilizing agent, wherein the permeabilizing agent is present in an amount effective to substantially enhance the permeability of the bladder wall to the clostridial derivative at a therapeutically effective rate, and without irreversibly damaging the bladder wall; and instilling the pharmaceutically composition to the bladder via a catheter; thereby alleviating the symptoms of the IC.

In another aspect, the present formulation maximizes the bioavailability of a clostridial derivative by preventing or minimizing the adsorption of the clostridial derivative to catheters, deliver device surfaces (syringe, patch, microneedle, engineered injector (Bioject, etc.), tubing and containers.

In another aspect, the present formulation maximizes the bioavailability of the clostridial derivative by enhancing the retention of the clostridial derivative to the skin or inner bladder wall surface, through mucoadhesive interactions.

Other Medical Disorders:

Treatment of Pain

In another embodiment, the present disclosure provides methods for treating pain comprising the step of administering a pharmaceutical formulation of the present invention to a subject in need thereof in an amount sufficient to reduce pain. In another embodiment, the patient suffers from myofascial pain, migraine headache pain, tension headache pain, neuropathic pain, facial pain, lower-back pain, sinus-headache pain, pain associated with temporomandibular joint disease, pain associated with spasticity or cervical dystonia, post-surgical wound pain, or neuralgia. A treatment session can comprise multiple treatments.

In an embodiment, the patient suffers from facial pain. A subject suffering from facial pain, for example, receives between about 4 to 40 U per treatment of a pharmaceutical formulation of the present disclosure. Dosages greater than 40 U per treatment may also be administered to patients with facial pain to achieve a therapeutic response. A treatment session can comprise multiple treatments.

In an embodiment, the patient suffers from myofascial pain. A subject suffering from myofascial pain, for example, receives between about 5 to 100 U per treatment of a pharmaceutical formulation of the present invention. Dosages greater than 100 U per treatment may also be administered to patients with myofascial pain to achieve a therapeutic response. A treatment session can comprise multiple treatments.

In an embodiment, the subject suffers from lower-back pain. A subject suffering from lower-back pain, for example, receives between about 15 to 150 U per treatment of a pharmaceutical formulation of the present invention. Dosages greater than 150 U per treatment may also be administered to patients with lower-back pain to achieve a therapeutic response. A treatment session can comprise multiple treatments.

In an embodiment, the patient suffers from migraine headache pain, including wherein the patient suffers from migraine headaches of 4 hours or more 15 or more days per month. A subject suffering from migraine-headache pain, for example, receives between about 0.5 to 200 U per treatment of a pharmaceutical formulation of the present invention. A treatment session can comprise multiple treatments.

For example, about 0.5 U, about 1.0 U, about 1.5 U, about 2.0 U, about 2.5 U, about 3.0 U, about 3.5 U, about 4.0 U, about 4.5 U, about 5.0 U, about 5.5 U, about 6.0 U, about 6.5 U, about 7.0 U, about 7.5 U, about 8.0 U, about 8.5 U, about 9.0 U, about 9.5 U, about 10.0 U, about 12 U, about 15 U, about 17 U, about 20 U, about 22 U, about 25 U, about 27 U, about 30 U, about 32 U, about 35 U, about 37 U, about 40 U, about 42 U, about 45 U, about 47 U, or about 50 U per treatment site are administered to a patient with migraine-headache pain. A patient can be treated at multiple sites, ranging from 2 sites up to 35 sites. In an embodiment, a patient suffering from migraine is a 31 times with 5 U per 0.1 mL injection, across the corrugator (2 injections of 5 U each), procerus (1 injection of 5 U), frontalis (4 injections of 5 U each), temporalis (8 injections of 5 U each), occipitalis (6 injections of 5 U each), cervical paraspinal (4 injections of 5 U each), and trapezius (6 injections of 5 U each) muscles. With the exception of the procerus muscle which can be injected at the midline, all muscles can, in certain embodiments, be injected bilaterally with half of the injection sites to the left and half to the right side of the head and neck. Dosages greater than 200 U per treatment may also be administered to patients with migraine-headache pain to achieve a therapeutic response. A treatment session can comprise multiple treatments. In alternative embodiments, the pharmaceutical composition is administered transdermally or topically.

In an embodiment, the patient suffers from sinus-headache pain. A subject suffering from sinus-headache pain, for example, receives between about 4 to 40 U per treatment of a pharmaceutical formulation of the present invention. In a further example, the subject receives between about 4 U to 40 U per treatment. Dosages greater than 40 U per treatment may also be administered to patients with sinus headache-pain to achieve a therapeutic response. A treatment session can comprise multiple treatments.

In an embodiment, the patient suffers from tension-headache pain. A subject suffering from tension-headache pain, for example, receives between about 5 to 50 U per treatment of a pharmaceutical formulation of the present invention. In an embodiment, a patient suffering from tension headache is injected 31 times with 5 U per 0.1 mL injection, across the corrugator (2 injections of 5 U each), procerus (1 injection of 5 U), frontalis (4 injections of 5 U each), temporalis (8 injections of 5 U each), occipitalis (6 injections of 5 U each), cervical paraspinal (4 injections of 5 U each), and trapezius (6 injections of 5 U each) muscles. With the exception of the procerus muscle which can be injected at the midline, all muscles can, in certain embodiments, be injected bilaterally with half of the injection sites to the left and half to the right side of the head and neck. Dosages greater than 200 U per treatment may also be administered to patients with tension headache pain to achieve a therapeutic response. A treatment session can comprise multiple treatments. In alternative embodiments, the pharmaceutical formulation may be administered topically or transdermally.

In an embodiment, the patient suffers from sinus headache pain or facial pain associated with acute or recurrent chronic sinusitis. For example a pharmaceutical formulation of the present invention can be administered to the nasal mucosa or to the subcutaneous structures overlying the sinuses, wherein the administration of the formulation reduces the headache and/or facial pain associated with acute recurrent or chronic sinusitis. In further embodiments, any of the pharmaceutical formulations of the present invention can be administered to the nasal mucosa or to the subcutaneous structures overlying the sinuses, such as over one or more of the sinuses selected from the group consisting of: ethmoid; maxillary; mastoid; frontal; and sphenoid. In another embodiment, subcutaneous structures overlying the sinuses lie within one or more of the areas selected from the group consisting of: forehead; malar; temporal; post auricular; and lip. In embodiments, multiple injections of 5 U each are administered to treat the sinus headache pain or facial pain associated with acute or recurrent chronic sinusitis.

In another embodiment, a patient suffering from sinus headache pain or facial pain associated with acute or recurrent chronic sinusitis is treated by administering any of the pharmaceutical formulations of the present invention to an afflicted area of the patient. In a further embodiment, the pharmaceutical formulations disclosed herein are administered to the projections of a trigeminal nerve innervating a sinus.

Patients suffering from sinus headache pain or facial pain associated with acute or recurrent chronic sinusitis often exhibit symptoms including rhinitis, sinus hypersecretion and/or purulent nasal discharge. In one embodiment, patients treated with the pharmaceutical formulations of the present invention exhibit symptoms of sinus hypersecretion and purulent nasal discharge.

Embodiments of the present disclosure also provide methods for treating a patient suffering from sinus headache pain or facial pain associated with acute or recurrent chronic sinusitis, wherein the subject suffers from neuralgia. In certain embodiments the neuralgia is trigeminal neuralgia. In another embodiment, the neuralgia is: associated with compressive forces on a sensory nerve; associated with intrinsic nerve damage, demyelinating disease, or a genetic disorder; associated with a metabolic disorder; associated with central neurologic vascular disease; or associated with trauma. In another embodiment of the present disclosure, the pain is associated with dental extraction or reconstruction.

EXAMPLES

The following examples illustrate embodiments and aspects of the present invention and are not intended to limit the scope of the present disclosure.

In the following examples, in addition to a botulinum toxin type A, BOTOX®, a TEM was used as an active pharmaceutical ingredient. In several examples, the TEM used comprised an opioid peptide targeting domain, or more specifically a nociceptin peptide. To facilitate screening of permeability enhancing vehicles in the in vitro 3D urothelial model, fluorescently labeled gelatin (100 kDa) was used as a surrogate (hereafter referred to as "surrogate"). The use of a fluorescent surrogate with similar molecular weight as the API to be delivered allowed the evaluation of the effects of exemplary permeabilizing agents on the bladder tissues by the use of fluorescence.

Example 1

Use of a human uroepithelial culture model to evaluate effect of exemplary agents on the permeation of human uroepithelial cells to a selected toxin, TEM, or surrogate fluorescent protein.

The effect of exemplary permeabilizing agents were evaluated in a human uroepithelial culture model as shown in FIG. 3.

A Human Uroepithelial Culture Model is shown in FIG. 3. Briefly, normal human bladder epithelial cells (CELLNTECH Cat # HBEP.05) were plated at a concentration of approximately 150,000 viable cells per well on either polyester (PET) or polycarbonate membrane inserts. The inserts were placed inside the wells of 24 well tissue culture plates. CELLNTECH CnT-58 media (growth media) was then added to the wells and the cells were incubated for 2 to 3 days at 37° C. (5% $CO_2$) until cells were confluent. At the end of incubation, growth media was removed and replaced with CELLNTECH CnT-21 media (differentiation media). Cells were then allowed to differentiate for 5 to 7 days after which a 2 to 3 cell human uroepithelial layer was established. BOTOX®, a TEM, or a biological surrogate (example 100 kDa Oregon Green 488 labeled Gelatin fluorescent gelatin) could then be formulated in test vehicle and applied to the membrane surface. The molecular weight of the fluorescent surrogate was chosen to represent a molecular weight close to the TEM and botulinum type A toxin. Typically a 0.1 mL volume of test solution was applied to the surface of the membrane inserts in which cells were grown on. Samples were then placed back into the incubator. At various time intervals flow through was collected in saline (example: Eagles Balanced Salt Saline Solution) or culture media (example: Eagle's Minimal Essential Medium). Typical sample collection intervals ranged from 1 to 3 hours. Other intervals (example: 24 hours) were sometimes collected. Samples were assayed after collection by measuring cell based potency (cell-based activity assays specific for BoNT/A or TEM), light chain cleavage of SNAPtide® 520 (HPLC Light Chain assay) or sample fluorescence.

The LC-HPLC assay has been previously described (Terrence Hunt, David Rupp, Gary Shimizu, Karen Tam, Julia Weidler and Jack Xie. Characterization of SNARE Cleavage Products Generated by Formulated Botulinum Neurotoxin Type-A Drug Products. Toxins 2010, 2, 2198-2212. The cell-based assay for BoNT/A has been previously described (Ester Fernandez-Salas, Joanne Wang, Yanira Molina, Jeremy B. Nelson, Birgitte P. S. Jacky, K. Roger Aoki. "Botulinum Neurotoxin Serotype A Specific Cell-Based Potency Assay to Replace the Mouse Bioassay". *PLoS One* (2012) art. no. e49516 and U.S. Pat. Nos. 8,198,034 & 8,361,789). The cell-based assay for TEM has been previously described in U.S. patent application US 20100233741. Each of the prior art disclosed herein is hereby incorporated by reference in its entirety.

Briefly, the light chain assay was carried out as follows: For each sample, a volume of 225 µl was transferred to separate reaction tubes (microcon tubes) containing 225 µL of 2× digestion buffer (see Table A for 2× digestion buffer composition). The samples were heated at 37° C. for 30 minutes (reduction step). After the completion of the reduction step, a volume of 25 µL of 200 µM SNAPtide® 520 was added to each tube (equivalent to 10.5 µM SNAPtide® 520). The reaction samples were then incubated at 30° C. for 20 hours (digestion step). At the completion of the digestion step, a volume of 25 µL of 5% trifluoroacetic acid (TFA) was added to each tube to stop the reaction. The contents of each tube were then transferred to HPLC vials for analysis.

TABLE A

| 2X Digestion Buffer Composition | |
|---|---|
| 2X Digestion Buffer | 1 mM $ZnCl_2$, 4 mM DTT[a], 0.1% TWEEN 20 in 100 mM HEPES, pH 7.4 |
| Substrate | 200 µM SNAPtide ® 520 prepared in SWFI[b] |

[a]Dithiothreitol
[b]List Biological Laboratories, Inc., supplied through Calbiochem (Cat# 567333)

The reaction solutions were analyzed via a reversed-phase high performance liquid chromatography method (RP-HPLC) using a Waters 2695 XE Separations Module and a Waters 2475 Multi λ Fluorescence Detector (see Table B for RP-HPLC parameters). The samples were eluted using a gradient program (see table C) with a mobile phase consisting of 0.1% TFA in water (A) and 0.1% TFA in acetonitrile (B). The data were collected and analyzed via Waters Empower™ Pro Software (Waters Corporation). The peak areas of the fluorescently labeled cleavage product (designated as SNAPtide® 529 by List Biological Laboratories, Inc.) obtained for the injected samples were compared.

TABLE B

| RP-HPLC Parameters | |
|---|---|
| Column | Waters Symmetry300 ™ C18, 3.5 µm, 4.6 × 150 mm (P/N: 186000197) |
| Column Temperature | 35° C. |
| Injection Volume | 25 µL |
| Flow | 1 mL/min |
| Detection | Excitation λ = 322 nm<br>Emission λ = 420 nm |

TABLE C

HPLC Gradient Program

| Time (min) | % A | % B |
|---|---|---|
| 0 | 90 | 10 |
| 5 | 90 | 10 |
| 13 | 85 | 15 |
| 18 | 5 | 95 |
| 20 | 5 | 95 |
| 21 | 90 | 10 |
| 30 | 90 | 10 |

Briefly, for the cell-based potency assay for BoNT/A SiMa H1 cells (Allergan, human neuroblastoma cell line) were utilized. For the TEM cell-based assay SiMa P33 hORL-1 stable cell line #6 (Allergan, human neuroblastoma cell line (SiMa P33, Allergan) transfected with human ORL-1 (hORL-1) plasmid (GeneCopoeia, EX-A1076-M-02, Germantown, Md.)). SiMa H1 clonal cell line or SiMa P33 hORL-1 stable cell line #6 were cultured in BD Biosciences brand 175 $cm^2$ Collagen IV flasks (62405-652, BD Biosciences, San Jose, Calif.) with vented caps. Growth media consisted of RPMI 1640, 0.1 mM Non-Essential Amino-Acids, 10 mM HEPES, 1 mM Sodium Pyruvate, 100 U/mL Penicillin, 100 µg/mL Streptomycin, and 10% Fetal Bovine Serum (FBS). All media components were obtained from Life Technologies. Differentiation medium consisted of Neurobasal® media, B27 supplement (1×), GlutaMax (1×), 100 U/mL Penicillin, and 100 µg/mL Streptomycin.

For the BoNT/A assay, SiMa H1 cells were plated in differentiation media at 100,000 cells per well in a 96 well plate for 3 days. Each well was treated for 24 h with 0.1 mL of the media removed from the bottom chamber from the permeability assay. The cells in 3 rows were also treated with BOTOX® resuspended in SWFI at doses from 0 to 300 Units per mL for 24 h as a reference using differentiation media as the diluent. For the TEM assay SiMa P33 hORL-1 #6 cells were plated in differentiation media at 50,000 cells per well in a 96 well plate for overnight. Each well was treated for 24 h with 0.1 mL of the media removed from the bottom chamber from the permeability assay. The cells in 3 rows were also treated with AGN-214868 (PRT-2623) at doses from 0 to 100 nM for 18 h as a reference.

After the treatment, the cells were cultured in differentiation media for an additional 3 days. The media was removed and the cells were lysed for 1 hour with 30 μL of lysis buffer consisting of 0.15 M sodium chloride, 20 mM Tris pH 7.5, 0.15 M sodium chloride, 1 nM EDTA, 1 mM EGTA, and 1% Triton X-100 in water. The lysates were centrifuged at 4000 rpm for 20 min to eliminate debris.

One microliter of the capture purified monoclonal antibody 2E2A6 (AGN) at 45 μg/mL in PBS containing 750 μg/mL of BSA was custom spotted on MSD High Bind plates by Meso Scale Discovery (MSD, Gaithersburg, Md., Cat # L11XB-3). The monoclonal antibody 2E2A6 developed by NTP specifically recognizes SNAP25$_{197}$. Plates were blocked with 150 μL Blocking Buffer consisting of 2% Amersham blocking reagent (GE-Healthcare, Piscataway, N.J., Cat# RPN418V), 10% goat serum (Rockland Inc, Cat # B304), in PBS-T (0.05% TWEEN 20 (BioRad, Hercules, Calif., Cat #161-0781) in PBS (GIBCO-Invitrogen, Cat#14040)) at room temperature for 1 hour, and the blocking buffer was then discarded.

Twenty five microliters of cell lysate were added to each well of the spotted MSD plate and the plate was incubated at 4° C. overnight. Plates were then washed three times with PBS-T. Twenty-five microliters of SULFO-TAG NHS-Ester labeled detection pAb anti-SNAP25 antibody (Ab to N-terminus of SNAP25 that recognizes uncleaved and cleaved products, Sigma, St. Louis, Mo., Cat# S9684) in 2% of Amersham blocking reagent in PBS-T at 5 μg/mL were added to the bottom corner of wells. Plates were sealed and shaken at room temperature for 1 h. Plates were washed three times with PBS-T, and 150 μL of 1× Read Buffer (MSD, Cat# R92TC-1) were added per well. Plates were read in the SI6000 Image reader (Meso Scale Discovery).

To demonstrate that the in-vitro 3D urothelium is impermeable, like the in vivo human urothelium, as is therefore amenable for screening of permeability enhancing vehicles, the surrogate fluorescent gelatin in saline was incubated for 1-3 hours in the upper compartment. Very low levels of fluorescent gelatin were recovered in the lower compartment demonstrating that the in vitro urothelium is impermeable to these high molecular weight proteins. Conversely, vehicles known to enhance permeability in vivo, like EDTA and Accutase, should cause the same effect in the in vitro urothelium. Accutase is a protease mixture that is typically used to harvest cells that are sensitive to treatment with trypsin. Accutase digest the tight junctions of HBEP cells, but it does not affect cell viability. An experiment was completed to measure the penetration of fluorescent gelatin when the in vitro urothelium is treated with Accutase or EDTA. After 5 minutes pretreatment with Accutase, the in vitro urothelium cell layer allowed 13,000% of the RFU than the untreated control; while the EDTA treated urothelium increased 300%. These data show that the in-vitro urothelium is an impermeable cell layer and that the permeability of the cell layer can be reversed.

Example 2

Triton X-100 and Nonoxynol 9 increased rat bladder permeation to a botulinum toxin type A, a TEM, and a fluorescent gelatin surrogate in a human uroepithelial culture model. In this example, effects of Triton X-100, Nonoxynol 9 and Poly-L-lysine Hydrobromide in the presence or absence of EDTA were evaluated.

The purpose of the study was to determine if the permeability of human uroepithelial cells to a TEM (100 kDa) could be increased if cells are pretreated for 30 minutes with solutions containing various permeabilization increasing agents. The following solutions were evaluated: saline, saline containing 50 mM EDTA, 1% Triton-X100 in saline, 1% Triton-X100 in saline containing 50 mM EDTA, 1% Nonoxynol 9 in saline, 1% Nonoxynol 9 in saline containing 50 mM EDTA, 1% Poly-L-lysine Hydrobromide in saline and 1% Poly-L-lysine Hydrobromide in saline containing 50 mM EDTA. A volume of 0.1 mL of each test solution was applied to the surface of the membrane inserts in which cells were grown on. Solutions were removed after 30 minutes incubation at 37° C. (5% $CO_2$). A volume of 0.1 mL saline containing 0.1 mg/mL TEM was then placed onto each membrane insert. Samples were then incubated for an additional 2 hours at 37° C. (5% $CO_2$). At 2 hours sample flow through was measured by the TEM cell based potency assay and by the HPLC Light Chain assay (Light chain cleavage of SNAPtide® 520), as described above.

As shown in FIG. 4, the results indicate that the permeability of human uroepithelial cells to fluorescent labeled TEM surrogate could be increased when cells were pretreated with Triton-X100, Nonoxynol 9 or Poly-L-lysine Hydrobromide. This enhancement occurred with or without EDTA.

Several other permeability enhancing vehicles were tested with the surrogate fluorescent gelatin and with TEM molecules. The results are summarized in Table D below:

TABLE D

| Vehicle | Description | Typical Results |
|---|---|---|
| SDS | Anionic surfactant | Inhibited |
| Protamine sulfate | Cationic | Inhibited |
| Benzalkonium bromide | Cationic | No Effect |
| Poloxamer 188 | Nonionic surfactant | Increase |
| Brij 97 (Polyoxyethylene (10) oleoyl ether) | Nonionic surfactant | Increase (Dose response) |
| Brij 98 (Polyoxyethylene (20) oleoyl ether) | Nonionic surfactant | Increase (Dose response) |
| Triton X | Nonionic surfactant | Increase (Dose response) |
| Nonoxynol 9 | Nonionic surfactant | Increase (Dose response) |
| Tween 20 | Nonionic surfactant | Increase (Dose response) |
| Tween 80 | Nonionic surfactant | Increase (Dose response) |
| Big Chaps | Nonionic surfactant | Increase (Dose response) |
| Deoxy Big Chaps | Nonionic surfactant | Increase (Dose response) |
| Polyethylene Glycol 3350 | Glycol | No Effect |
| Benzyl Alcohol | Preservative | Slight Increase (1% at 2 and 3 hours) |
| Chitosan | Microadhesive | Inhibited |
| Diethylene glycol mono-ethyl ether | Glycol | No Effect |
| Revance Peptide | Cell-penetrating peptide | No Effect at 1 through 3 hours |
| Poly-L-Lysine | Peptide | Increase (Dose response) |
| Poly-L-Arginine | Peptide | Inhibited |
| EDTA | Chelator | Increase |

Example 3

Time and agent concentration dependent transport of fluorescent gelatin surrogate through the human uroepithelial cells. (FIGS. 5A and 5B)

Briefly, in this example, human uroepithelial cells were exposed to various vehicles containing Oregon Green 488 fluorescent labeled gelatin at a concentration of 0.1 mg/mL. The test vehicles consisted of the following: saline, 0.00745% Triton-X100 in saline, 0.0149% Triton-X100 in saline, 0.0745% Triton-X100 in saline, 0.149% Triton-X100 in saline, 0.745% Triton-X100 in saline, 0.00262% Nonoxynol 9 in saline, 0.00524% Nonoxynol 9 in saline, 0.0262% Nonoxynol 9 in saline, 0.0524% Nonoxynol 9 in saline, 0.262% Nonoxynol 9 in saline and 0.524% Nonoxynol 9 in saline. Each sample is also expressed as a multiple of the critical micelle concentration (CMC) of Triton-X100 or Nonoxynol 9. The CMC can be defined as the concentration of surfactant above which micelles are spontaneously formed. One hundred microliter volume of each test solution was applied to the surfaces of the membrane inserts in which cells were grown on. Cells were incubated at 37° C. (5% $CO_2$). At 1, 2 and 3 hours sample flow through was sampled and measured for relative fluorescence.

As shown in FIGS. 5A and 5B, the results demonstrate that transport is both concentration and time dependent. Increased transport was seen when increasing surfactant concentration and with increased incubation time. Increased transport was observed for each surfactant vehicle above its CMC.

Example 4

Effects of exemplary permeabilizing agents on the permeability of human uroepithelial cells to a botulinum toxin complex (FIGS. 6A and 6B)

The purpose of the study was to determine if the permeability of human uroepithelial cells to BOTOX® (botulinum type A toxin complex) could be increased if applied in vehicles containing various concentrations of Triton-X100 (FIG. 6A) or Nonoxynol 9 (FIG. 6B). The following test vehicles were evaluated: sterile water for injection, 0.01% Triton-X100 in sterile water for injection, 0.025% Triton-X100 in sterile water for injection, 0.05% Triton-X100 in sterile water for injection, 0.01% Nonoxynol 9 in sterile water for injection, 0.025% Nonoxynol 9 in sterile water for injection and 0.05% Nonoxynol 9 in sterile water for injection. Because each BOTOX® vial contains 0.9 sodium chloride, sterile water for injection was used to prepare the vehicles in order to maintain 0.9% sodium chloride solutions after reconstitution (0.1 mL reconstitution volume). Vials of 100 unit BOTOX® were reconstituted with 0.1 mL volumes of each vehicle. The resulting solutions contain 1000 BOTOX® units per milliliter. A volume of 0.1 mL of each reconstituted solution was applied to the surfaces of the membrane inserts in which cells were grown on. At 1 and 3 hours sample flow through was measured by the HPLC Light Chain assay (Light chain cleavage of SNAPtide® 520) and the BoNT/A cell-based assay.

The results shown in FIGS. 6A and 6B demonstrate that permeability of human uroepithelial cells to BOTOX® (botulinum type A toxin complex) could be increased when applied in vehicles containing Triton-X100 (FIG. 6A), and Nonoxynol 9 (FIG. 6B). Test results demonstrate that permeability is both concentration and time dependent. Increased permeability was seen when increasing Triton-X100 and Nonoxynol 9 concentration and with increased time (1 hour versus 3 hours). Increased permeability is reflected in the increases seen in peak area counts (Snaptide® 520 cleavage).

The sample flow through at 1 hour was also analyzed in the BoNT/A cell-based assay. There was a 3 fold increase vs saline in the amount of BoNT/A that permeated the in vitro urothelium when BOTOX® was administered in the presence of 0.05% Nonoxynol 9, and a 3.6 fold increase vs. saline when 0.05% Triton-X100 was used.

It has been reported that at a pH value of 6 the 900 kDa botulinum type A toxin complex will remain intact while at a pH value of 8 the complex will disassociate resulting in free 150 kDa botulinum type A toxin (1). The following test solutions were evaluated: 5 mM potassium phosphate saline, pH 6.0; 5 mM potassium phosphate saline, pH 8.0; 0.5% Triton-X100 in 5 mM potassium phosphate saline, pH 6.0 and 0.5% Triton-X100 in 5 mM potassium phosphate saline, pH 8.0. The sample flow through was assayed in the BoNT/A cell-based assay. There were no differences between BOTOX® in pH 6 or 8, and in both cases, the use of 0.5% Triton-X100 increased the permeability of active BoNT/A through the in vitro urothelium (FIG. 7).

Example 5

In vivo assessment: Effect of exemplary permeabilizing agents was evaluated in vivo on rat bladder. In this example, effects of Triton X-100 and Nonoxynol 9 were evaluated (FIGS. 8A, 8B, 9A and 9B)

Methods:

BOTOX® and TEM Surrogate Administration:

For instillation of vehicle control, working solutions of BOTOX® (onabotulinumtoxinA; Allergan) and the surrogate were prepared in either 0.9% saline or 0.5% HSA, respectively. For instillation of the surfactant, working solutions of BOTOX® (onabotulinumtoxinA; Allergan) and TEM surrogate were prepared in 0.9% saline. The urinary bladder wall was instilled with BOTOX® (20 U) or surrogate (250 µg) for 1 hour, under anesthesia. All in vivo protocols and procedures were approved by the institutional AACUC.

Tissue Preparation:

Bladder tissue from adult Sprague Dawley rats (220-250 g, n=2-20) were harvested 2-days post-instillation and fixed overnight at 4° C. in Zamboni's fixative. Tissues were then cryoprotected (30% sucrose), hemisected longitudinally, frozen in embedding medium and kept at −80° C. until use.

Immunofluorescence:

One tissue block per animal was cryostat-sectioned (14 µm-thick) in the longitudinal plane and slide-mounted. Three slides were prepared from each block, with three sections on each slide, approximately 140 µm apart. Two slides were processed for immunofluorescence. Tissue sections were first blocked for non-specific signal in blocking buffer (1×PBS+0.1% Triton X-100+10% Normal Donkey Serum) and then incubated with combinations of primary antibodies at the desired concentration in blocking buffer, overnight at 4° C. The primary antibodies used were as follows: mouse anti-Calcitonin-Gene-Related-Peptide (CGRP; Sigma, C7113, 1:5,000), anti-cleaved SNAP25 ($SNAP25_{197}$; Allergan, 1:1,000), rabbit anti-synaptic vesicle glycoprotein 2C (SV2C; Santa Cruz Biotechnologies, sc-28957, 1:800) and rabbit anti-vesicular acetylcholine transporter (VAChT; Sigma, V5387, 1:3,000). Following washes, sections were incubated with secondary antibodies (Jackson ImmunoResearch) for 2 hours at 4° C. and then washed again. Slide-mounted sections were cover slipped using Fluor mount-G with 1.5 µg/ml DAPI. The third slide was stained with Hematoxylin & Eosin (H&E) for anatomical assessment.

Data Analysis and Quantitation:

Images were analyzed and captured on either a Leica DMLB brightfield microscope, a Nikon E800 fluorescent wide field microscope or a Zeiss LSM-710 confocal microscope using Image-Pro® (MediaCybernetics), Metamorph® (Molecular Devices) or ZEN (Carl Zeiss) software. Imaris® (Bitplane) software was used for high-resolution, 3D qualitative analysis to establish the spatial relationships of nerve fibers. Nerve fiber-types were identified on the basis of their morphology and neurochemistry. For the semi-quantitative analysis, for each slide, all 3 sections were carefully observed under a microscope and a score (from 0 to 5) was given for each animal on either the extent of $SNAP25_{197}$ staining (as shown in FIG. 8A) or on the integrity of the bladder anatomy (H&E) (as shown in FIG. 8B). An average score was calculated for each treatment/formulation and the results are presented as a bar graph (FIGS. 9A, 9B).

FIG. 8A shows a Semi-quantitative assessment of rat bladder integrity using an ordinal scoring method of 0-5; '0' being a normal bladder and '5' showing severe pathology.

FIG. 8B shows a Semi-quantitative assessment of the extent of SNAP25-197 staining corresponding to VAChT staining of parasympathetic nerve fibers in rat bladder using an ordinal scoring method of 0-5; '0' being no SNAP25-197 staining detected and '4.5' showing near complete overlap of both biomarkers. A score of '5' was never observed.

FIG. 9A shows the extent of SNAP25-197 staining (blue bars) and bladder tissue damage based on H&E staining (red bars) following surrogate (250 µg) bladder instillation along with increasing concentrations of surfactant. Values are means±SD for the given number of animals. *P<0.05 significantly different from vehicle control by one-way ANOVA followed by Holm-Sidak post-hoc analysis.

FIG. 9B shows the extent of SNAP25-197 staining (blue bars) and bladder tissue damage based on H&E staining (red bars) following surrogate (250 µg) or BOTOX® (20 U) instillation along with increasing concentrations of surfactant into rat bladders from interstitial cystitis model. Values are means±SD for the given number of animals. *P<0.05 significantly different from vehicle control by one-way ANOVA followed by Holm-Sidak post-hoc analysis.

Example 6

Effect of Triton-X100 on the permeability of the bladder wall to intact 900 kDa botulinum type A complex and free 150 botulinum type A. (FIG. 10)

It has been reported that at a pH value of 6 the 900 kDa botulinum type A toxin complex will remain intact while at a pH value of 8 the complex will disassociate resulting in free 150 kDa botulinum type A toxin (1). The following test solutions were evaluated: 5 mM potassium phosphate saline, pH 6.0; 5 mM potassium phosphate saline, pH 8.0; 0.1% Triton-X100 in 5 mM potassium phosphate saline, pH 6.0 and 0.1% Triton-X100 in 5 mM potassium phosphate saline, pH 8.0. A volume of 2.5 mL of each solution was used to reconstitute 100 unit BOTOX® vials. This resulted in 40 unit per milliliter solutions. A volume of 0.5 mL of each reconstituted solution was instilled into rat bladders resulting in the instillation of 20 units.

FIG. 10 shows the extent of SNAP25-197 staining (blue bars) and bladder tissue damage based on H&E staining (red bars) following BOTOX® (20 U) bladder instillation at either pH 6.0 or pH 8.0 in saline or surfactant. Values are means±SD for the given number of animals. *P<0.05 significantly different from vehicle control at given pH by t-test analysis.

Example 7

Effect of an exemplary permeabilizing agent on human bladder cell mucoadhesive retention. In this example, the exemplary permeabilizing agent is Chitosan (FIG. 11)

Chitosan Demonstrating Human Bladder Cell Mucoadhesive Retention

Human bladder cells (CELLNTECH Cat#HBEP.05 were plated at 150,000 cells per well on PET membrane inserts (24 well) in CELLNTECH CnT-58 media (growth media) for 3 days, then in CELLNTECH CnT-21 (differentiation media) for 7 days. Cell layer preconditioned in Saline with 0%, 0.025%, 0.05%, 0.1%, 0.2%, 0.4% Chitosan or for 10 minutes with Accutase (mild Trypsin)

Cell layer treated with 100 µL 0.5 mg/mL Oregon Green labeled Gelatin.

Flow Through media was Hanks Balanced Salt Saline Solution.

Flow through media was collected and RFU was measured at 30 min, 1 hour, 2 hour, and 3 hour.

The amount remaining on membrane visualized and counted, the results are shown in FIG. 11. The results show that chitosan increased the retention of gelatin within the in vitro urothelium.

Example 8

Triton X-100 induced increased permeability of the bladder wall was reversible

Human bladder uroepithelial cells (CELLnTEC Cat # HBEP.05) were plated at a concentration of approximately 150,000 viable cells per well on polycarbonate membrane inserts. The inserts were placed inside the wells of 24 well tissue culture plates. CELLnTEC CnT-58 media (growth media) was then added to the wells and the cells were incubated for 2 days at 37° C. (5% $CO_2$) until cells were confluent. At the end of incubation, growth media was removed and replaced with CELLnTEC CnT-21 media (differentiation media). Cells were then allowed to differentiate for 7 days after which a 2 to 3 cell human uroepithelial layer was established. Cells were treated for one hour with the following vehicles: 0.9% saline, 0.1% Triton X-100 in 0.9% saline and 0.5% Triton X-100 in saline. Each vehicle was tested in triplicate. Cells were treated by applying 0.1 mL volumes of each vehicle to the surfaces of the membrane inserts in which cells were grown on. After exposure vehicle solutions were removed from the inserts and differentiation media was added to each insert. Cells were then incubated and allowed to recover for either 0, 24, or 48 hours. Note that 0.9% saline (negative control) was only tested at 0 hours. Gelatin permeability assays were then performed. Gelatin permeability assays were performed by removing media from each insert followed by adding 0.1 mL volumes of 0.1 mg/mL Oregon Green 488 labeled gelatin, formulated in saline, to each insert. Inserts were placed into wells containing 0.8 mL volumes of Earl's Balanced Salt Solution. After 1 hour exposure, flow through was collected and measured for fluorescence using an Envision instrument. Twenty-four hour and forty-eight hour test results were then compared to 0 hour data to determine if decreases in gelatin permeability had occurred.

It was found that the amount of gelatin that diffused through the in vitro urothelium treated with 0.1% Triton X-100 was lower after 24 and 48 hours recovery. These results suggest recovery of in vitro human urothelial permeability after treatment with 0.1% Triton X-100.

Example 9 (FIGS. 12, 13, 14A-14D and 15)

The purpose of this study was to evaluate the effect of botulinum toxin type A, known as BOTOX®, in one of eight vehicle formulations administered by instillation into the urinary bladder of female Sprague Dawley rats. The effect was examined eight days after administration wherein efficacy and tolerability were evaluated by immunohistochemistry (IHC) and histopathology, respectively.

Positive Controls:

Four rats were administered 10 units of BOTOX® in saline by injection into the detrusor muscle.

Negative Controls:

Formulations containing the vehicle only (as shown in Table 1 without addition of) BOTOX®.

Cleaved SNAP 25 was used as a biomarker of BOTOX® activity at synaptic terminals and a potential indicator of functionality of the method of delivery. In this study it was used to confirm the successful movement of BOTOX® across the urothelium. Synaptophysin expression was used to identify synaptic terminals and to ensure specificity of cleaved SNAP 25 localization. Histopathology was done to assess impact of the formulation on the bladder tissue.

Female rats weighing between 150-200 grams were administered 0.5 ml vehicle formulation or vehicle formulation+30 U Botox® according to Table 1:

TABLE 1

| UR13002RS Study Number | DP Study Number | Vehicle Formulation |
|---|---|---|
| 1 | DP13104 | 0.1% Triton |
| 2 | DP13112 | 0.2% Triton |
| 3 | DP13117 | 0.05% Triton |
| 4 | DP13121 | 0.1% Nonoxynol-9[a] |
| 5 | DP13129 | 1% Chitosan + 0.1% Triton |
| 6 | DP13130 | 0.25% HPMC + 0.1% Triton |
| 7 | DP13139 | 0.1% Tyloxapol |
| 8 | DP13145 | 1% Chitosan + 0.1% Nonoxynol-9 |

[a]= only 5 vehicle + BOTOX treated bladders submitted for evaluation.

Intravesical instillation of the formulation was caned out as follows: rats were anesthetized with isoflurane and the bladder emptied by way of finger tip pressure applied on the lower abdomen. While under anesthesia, a catheter was introduced into the urinary bladder via the urethra. Subsequently, the formulation was slowly administered over a course of two minutes into the urinary bladder at a dose volume of 0.5 ml+0.1 ml (to accommodate for the dead space created by the catheter). The formulation was allowed to dwell in the bladder for 60 minutes before anesthesia recovery. The rats were euthanized one week after instillation.

Urinary bladders were collected, fixed in 10% formalin and processed using standard histological techniques. Additional sections were prepared and processed for fluorescent immunohistochemistry for cleaved SNAP 25 and synaptophysin.

Immunofluorescence:

One tissue block per animal was cryostat-sectioned (14 μm-thick) in the longitudinal plane and slide-mounted. Three slides were prepared from each block, with three sections on each slide, approximately 140 μm apart. Two slides were processed for immunofluorescence. Tissue sections were first blocked for non-specific signal in blocking buffer (1×PBS+0.1% TX-100+10% Normal Donkey Serum) and then incubated with combinations of primary antibodies at the desired concentration in blocking buffer, overnight at 4° C. The primary antibodies used were as follows: mouse anti-Calcitonin-Gene-Related-Peptide (CGRP; Sigma, C7113, 1:5,000), anti-cleaved SNAP25 ($SNAP25_{197}$; Allergan, 1:1,000), rabbit anti-synaptic vesicle glycoprotein 2C (SV2C; Santa Cruz Biotechnologies, sc-28957, 1:800) and rabbit anti-vesicular acetylcholine transporter (VAChT; Sigma, V5387, 1:3,000). Following washes, sections were incubated with secondary antibodies (Jackson ImmunoResearch) for 2 hr at 4° C. and then washed again. Slide-mounted sections were coversliped using Fluoromount-G with 1.5 μg/ml DAPI. The third slide was stained with Hematoxylin & Eosin (H&E) for anatomical assessment.

Data Analysis and Quantitation:

Images were analyzed and captured on either a Leica DMLB brightfield microscope, a Nikon E800 fluorescent widefield microscope or a Zeiss LSM-710 confocal microscope using Image-Pro®, (MediaCybernetics), Metamorph® (Molecular Devices) or ZEN (Carl Zeiss) software. Imaris® (Bitplane) software was used for high-resolution, 3D qualitative analysis to establish the spatial relationships of nerve fibers. Nerve fiber-types were identified on the basis of their morphology and neurochemistry For the semi-quantitative analysis, for each slide, all 3 sections were carefully observed under a microscope and a score (from 0 to 4) was given for each animal on either the extent of $SNAP25_{197}$ staining (as shown in FIGS. 12 and 13) or on the integrity of the bladder anatomy (H&E) (as shown in FIGS. 14A-D). An average score was calculated for each treatment/formulation and the results are partly presented in Table 2 and FIG. 15.

The formulations were evaluated based on the following:

1. Histological changes in the bladder wall; wherein a diagnosis of "spindle cell infiltrate" was made for bladders in which an increased number of fusiform cells of indeterminant origin were found infiltrating the lamina propria (FIGS. 14B, 14C and 14D); as a reactive change, these were considered undesirable as a potential precursor to fibrosis; and
2. Cleaved SNAP 25 score.

Summary of Results:

The results are summarized in Table 2.

TABLE 2

| | Rat # | Treatment | WNL | infiltrates/inflammation: lamina propria | spindle cell infiltrates | edema | other | cleaved SNAP 25 |
|---|---|---|---|---|---|---|---|---|
| UR13002RS1/ DP13104 | | | | | | | | |
| 150 | 1 | 0.1% Triton + BTX (30 U) Installation | x | | | | | 2 |
| 250 | 2 | 0.1% Triton + BTX (30 U) Installation | | min monomuclear infiltrates | | | | 0 |
| 350 | 3 | 0.1% Triton + BTX (30 U) Installation | | min mixed cell infiltrates | min, lamina propria | | | 3 |
| 450 | 4 | 0.1% Triton + BTX (30 U) Installation | x | | | | | 1 |
| 550 | 5 | 0.1% Triton + BTX (30 U) Installation | x | | | | | 0 |
| 650 | 6 | 0.1% Triton + BTX (30 U) Installation | x | | | | | 2 |
| 750 | 7 | 0.1% Triton Installation | | min monomuclear infiltrates | | | | 0 |
| 850 | 8 | 0.1% Triton Installation | x | | | | | 0 |
| UR13002RS2/ DP13112 | | | | | | | | |
| 150 | 10 | 0.2% Triton Installation | | min monomuclear infiltrate | | | | 0 |
| 250 | 11 | 0.2% Triton + BTX (30 U) Installation | | min mixed cell infiltrates | | | | 2 |
| 350 | 12 | 0.2% Triton + BTX (30 U) Installation | | min monomuclear cell infiltrates | min, lamina propria | | | 3 |
| 450 | 13 | 0.2% Triton + BTX (30 U) Installation | | mild mixed cell inflammation | mild, lamina propria | | | 2 |
| 550 | 14 | 0.2% Triton + BTX (30 U) Installation | | mild mixed cell inflammation | mild, lamina propria | | | 3 |
| 650 | 15 | 0.2% Triton + BTX (30 U) Installation | | min mixed cell infiltrates | min, lamina propria | | | 2 |
| 750 | 16 | 0.2% Triton + BTX (30 U) Installation | | | | | | 2 |
| 850 | 17 | 0.2% Triton + BTX (30 U) Installation | | min monomuclear cell infiltrates | min, lamina propria | | | 2 |
| | 18 | 0.2% Triton Installation | x | | | | | 0 |
| UR13002RS3/ DP13117 | | | | | | | | |
| 150 | 19 | 0.05% Triton + BTX (30 U) Installation | x | | | | | 0 |
| 250 | 20 | 0.05% Triton Installation | | minimal mixed cell inflammation | mild | | | 0 |
| 350 | 21 | 0.05% Triton Installation | x | | | | | 0 |
| 450 | 22 | 0.05% Triton + BTX (30 U) Installation | | minimal mixed cell inflammation | mild | | focal lesion | 1 |
| 550 | 23 | 0.05% Triton + BTX (30 U) Installation | | moderate mixed cell inflammation | mod | | | 1 |
| 650 | 24 | 0.05% Triton + BTX (30 U) Installation | | moderate mixed cell inflammation | mod | mild | | 1 |
| 750 | 25 | 0.05% Triton + BTX (30 U) Installation | | | | | | 1 |
| 850 | 26 | 0.05% Triton + BTX (30 U) Installation | x | | mod | moderate | ulceration | 2 |
| UR13002RS4/ DP13121 | | | | | | | | |
| 150 | 27 | 0.1% Nonoxynol-9 | | minimal mixed cell inflammation | min, lamina propria | | | 0 |
| 250 | 29 | 0.1% Nonoxynol-9 + 30 U Botox | | minimal monomuclear infiltrates | min, lamina propria | | | 2 |
| 350 | 30 | 0.1% Nonoxynol-9 + 30 U Botox | | minimal mized cell infiltrates | | | | 3 |
| 450 | 31 | 0.1% Nonoxynol-9 + 30 U Botox | | minimal mononuclear infiltrates | min, lamina propria | | patchy | 2 |
| 550 | 32 | 0.1% Nonoxynol-9 + 30 U Botox | x | | | | | 2 |
| 650 | 33 | 0.1% Nonoxynol-9 + 30 U Botox | x | | | | | 3 |
| 750 | 34 | 0.1% Nonoxynol-9 | | mild mixed cell inflammation | min, lamina propria | | diffuse; hemorrhage | 0 |
| UR13002RS8/ DP13129 | | | | | | | | |
| 150 | 35 | 1% Chitosan + 0.1% triton + 30 U Botox | | min monomuclear infiltrate | | | | 2 |
| 250 | 36 | 1% Chitosan + 0.1% triton + 30 U Botox | | min monomuclear infiltrate | | | | 3.5 |

TABLE 2-continued

| | Rat # | Treatment | WNL | infiltrates/inflammation: lamina propria | spindle cell infiltrates | edema | other | cleaved SNAP 25 |
|---|---|---|---|---|---|---|---|---|
| 350 | 37 | 1% Chitosan + 0.1% triton + 30 U Botox | | minimal mixed cell inflammation | | | focal epithelium hyperplasia, min | 3.5 |
| 450 | 38 | 1% Chitosan + 0.1% triton + 30 U Botox | | min mononuclear infiltrate | | | | 3 |
| 550 | 39 | 1% Chitosan + 0.1% triton + 30 U Botox | | mild mononuclear infiltrates | | | | 3 |
| 650 | 40 | 1% Chitosan + 0.1% triton | x | | | | | 0 |
| 750 | 41 | 1% Chitosan + 0.1% triton + 30 U Botox | | mild mononuclear inflammation | | | | 4 |
| 850 | 42 | 1% Chitosan + 0.1% triton | | minimal mixed cell inflammation/mononuclear infiltrate | | | | 0 |
| UR13002RS6/ DP130130 | | | | | | | | |
| 150 | 43 | 0.25% HPMC + 0.1% Triton + BTX (30 U) Installation | x | | | | | 3 |
| 250 | 44 | 0.25% HPMC + 0.1% Triton + BTX (30 U) Installation | | mod mixed cell inflammation | mild | mild | | 2 |
| 350 | 45 | 0.25% HPMC + 0.1% Triton | | mod mixed cell inflammation | mild | mild | mild hemorrhage | 0 |
| 450 | 46 | 0.25% HPMC + 0.1% Triton + BTX (30 U) Installation | x | | | | | 2 |
| 550 | 47 | 0.25% HPMC + 0.1% Triton + BTX (30 U) Installation | | mod mixed cell inflammation | mild | mild | | 1 |
| 650 | 48 | 0.25% HPMC + 0.1% Triton + BTX (30 U) Installation | | min mixed cell inflammation | min | | | 2 |
| 750 | 49 | 0.25% HPMC + 0.1% Triton + BTX (30 U) Installation | x | | | | | 2 |
| 850 | 50 | 0.25% HPMC + 0.1% Triton | | severe mixed cell inflammation | mild | mod | large ulcer; bacteria | 0 |
| UR13002RS8/ DP13145 | | | | | | | | |
| 150 | 59 | 1% Chitosan + 0.1% Nonoxynol-9 + BTX (30 U) | | min mononuclear cell infiltrate | | | | 1 |
| 250 | 60 | 1% Chitosan + 0.1% Nonoxynol-9 + BTX (30 U) | | mild mononuclear cell infiltrate | min | | | 1 |
| 350 | 61 | 1% Chitosan + 0.1% Nonoxynol-9 + BTX (30 U) | | mild mononuclear cell infiltrate | min | | degranulated cells | 2 |
| 450 | 62 | 1% Chitosan + 0.1% Nonoxynol-9 | x | | | | | 0 |
| 550 | 63 | 1% Chitosan + 0.1% Nonoxynol-9 + BTX (30 U) | | mild mixed cell inflammation | mild | | | 1 |
| 650 | 64 | 1% Chitosan + 0.1% Nonoxynol-9 + BTX (30 U) | | min mononuclear cell infiltrate | | | | 2 |
| 750 | 65 | 1% Chitosan + 0.1% Nonoxynol-9 | x | | | | | 0 |
| 850 | 66 | 1% Chitosan + 0.1% Nonoxynol-9 + BTX (30 U) | | mild mixed cell inflammation | mild | | | 3 |
| UR13002RS7/ DP13139 | | | | | | | | |
| 150 | 51 | 0.1% Tyloxapol + 30 U Botox | x | | | | | 1 |
| 250 | 52 | 0.1% Tyloxapol + 30 U Botox | x | | | | | 0 |
| 350 | 53 | 0.1% Tyloxapol + 30 U Botox | x | | | | | 0 |
| 450 | 54 | 0.1% Tyloxapol + 30 U Botox | x | | | | | 0 |
| 550 | 55 | 0.1% Tyloxapol + 30 U Botox | x | | | | | 0 |
| 650 | 56 | 0.1% Tyloxapol + 30 U Botox | x | | | | | 0 |
| 750 | 57 | 0.1% Tyloxapol | | mod mixed cell | | mod | | 0 |
| 850 | 58 | 0.1% Tyloxapol | x | | | | | 0 |
| 950 | 1 | 0.9% saline + 10 U Botox | | | | | ulcer | 4 |
| 951 | 2 | 0.9% saline + 10 U Botox | | | | | min mixed inflammation, | 2 |
| 952 | 3 | 0.9% saline + 10 U Botox | | | | | min mixed inflammation, | 3 |
| 953 | 4 | 0.9% saline + 10 U Botox | | | | | mod granulomatous | 1 |

Test formulations: Positive immunohistochemistry scores were observed in all samples post intravesical instillation of BOTOX®, except for the formulations of 0.1% (w/v) Tyloxapol. FIG. 15 shows the IHC scores of some exemplary formulations.

Example 10

Treatment of Overactive Bladder

This example describes treatment of patients with hyper reflexive bladder due to neurogenic or idiopathic bladder dysfunction.

Several patients with hyper reflexive bladders symptoms (bladder infection, incontinence, and urge incontinence) due to neurogenic or idiopathic bladder dysfunction are treated by bladder instillation. A pharmaceutical composition comprising about 100 Units of BOTOX®, 0.1% (w/v) Triton™ X-100 and 1% (w/v) chitosan. The pharmaceutical composition is instilled to the bladder of the patients while under light sedation. A significant increase in mean maximum bladder capacity and a significant decrease in mean maximum detrusor voiding pressure are observed 7 days post treatment.

Many alterations and modifications may be made by those having ordinary skill in the art, without departing from the spirit and scope of the disclosure. Therefore, it must be understood that the described embodiments have been set forth only for the purposes of examples, and that the embodiments should not be taken as limiting the scope of the following claims. The following claims are, therefore, to be read to include not only the combination of elements which are literally set forth, but all equivalent elements for performing substantially the same function in substantially the same way to obtain substantially the same result. The claims are thus to be understood to include those that have been described above, those that are conceptually equivalent, and those that incorporate the ideas of the disclosure.

We claim:

1. A pharmaceutical composition comprising a therapeutically effective amount of a clostridial derivative and at least one permeabilizing agent, wherein:
   the at least one permeabilizing agent is present in an amount effective to substantially and reversibly increase the permeability of the bladder wall to the clostridial derivative;
   the clostridial derivative is a botulinum toxin;
   the at least one permeabilizing agent comprises a surfactant and a mucoadhesive;
   the surfactant is present in an amount of about 0.1% (w/v);
   the mucoadhesive comprises chitosan; and
   the surfactant comprises octoxynol-9.

2. The pharmaceutical composition of claim 1, wherein the mucoadhesive is present in an amount ranging from about 0.01% to about 5% (w/v).

3. The pharmaceutical composition of claim 1, wherein the mucoadhesive is present in an amount of about 1% (w/v).

4. The pharmaceutical composition of claim 1, wherein the clostridial derivative is a botulinum toxin type A.

5. The pharmaceutical composition of claim 1, wherein the surfactant is present in an amount of 0.1% (w/v).

6. A method of treating a neurogenic bladder dysfunction in a patient in need thereof, comprising intravesically instilling to the bladder wall of the patient a pharmaceutical composition, wherein:
   the pharmaceutical composition comprises a therapeutically effective amount of a clostridial derivative and at least one permeabilizing agent present in an amount effective to substantially increase the permeability of the bladder wall to the botulinum neurotoxin at a therapeutically effective rate;
   the clostridial derivative is a botulinum toxin;
   the at least one permeabilizing agent comprises a surfactant and a mucoadhesive;
   the surfactant is present in an amount of about 0.1% (w/v);
   the mucoadhesive comprises chitosan; and
   the surfactant comprises octoxynol-9.

7. A pharmaceutical composition comprising a therapeutically effective amount of a clostridial derivative and at least one permeabilizing agent, wherein:
   the at least one permeabilizing agent is present in an amount of 0.005-10% (w/v) to substantially and reversibly increase the permeability of the bladder wall to the clostridial derivative;
   the clostridial derivative is a botulinum toxin;
   the at least one permeabilizing agent comprises a surfactant and a mucoadhesive;
   the surfactant is octoxynol-9; and
   the mucoadhesive is chitosan.

8. The composition of claim 7, wherein the surfactant is present at about 0.1% (w/v) and the mucoadhesive is present at about 1% (w/v).

9. A method of treating a neurogenic bladder dysfunction in a patient in need thereof, comprising intravesically instilling to the bladder wall of the patient a pharmaceutical composition of claim 7.

* * * * *